(12) United States Patent
Wynberg

(10) Patent No.: US 8,888,787 B2
(45) Date of Patent: Nov. 18, 2014

(54) PERCUTANEOUS RENAL ACCESS SYSTEM

(75) Inventor: Jason Benjamin Wynberg, Oak Park, MI (US)

(73) Assignee: JBW7 Innovations, LLC, Southfield, MI (US)

( * ) Notice: Subject to any disclaimer, the term of this patent is extended or adjusted under 35 U.S.C. 154(b) by 261 days.

(21) Appl. No.: 13/430,747

(22) Filed: Mar. 27, 2012

(65) Prior Publication Data

US 2012/0203064 A1 Aug. 9, 2012

Related U.S. Application Data

(63) Continuation-in-part of application No. 13/291,927, filed on Nov. 8, 2011, now Pat. No. 8,771,287.

(60) Provisional application No. 61/498,644, filed on Jun. 20, 2011, provisional application No. 61/498,393, filed on Jun. 17, 2011, provisional application No. 61/496,950, filed on Jun. 14, 2011, provisional application No. 61/475,318, filed on Apr. 14, 2011, provisional application No. 61/473,906, filed on Apr. 11, 2011, provisional application No. 61/446,294, filed on Feb. 24, 2011, provisional application No. 61/413,598, filed on Nov. 15, 2010, provisional application No. 61/413,977, filed on Nov. 15, 2010, provisional application No. 61/413,981, filed on Nov. 15, 2010, provisional application No. 61/413,993, filed on Nov. 16, 2010, provisional application No. 61/421,071, filed on Dec. 8, 2010, provisional application No. 61/422,202, filed on Dec. 12, 2010, provisional application No. 61/424,041, filed on Dec. 16, 2010, provisional application No. 61/570,987, filed on Dec. 15, 2011, provisional application No. 61/563,969, filed on Nov. 28, 2011, provisional application No. 61/588,509, filed on Jan. 19, 2012, provisional application No. 61/597,828, filed on Feb. 12, 2012, provisional application No. 61/600,936, filed on Feb. 20, 2012.

(51) Int. Cl.
*A61F 11/00* (2006.01)
*A61B 1/018* (2006.01)
*A61B 17/34* (2006.01)
*A61B 17/22* (2006.01)
*A61M 25/01* (2006.01)
*A61M 25/09* (2006.01)
*A61M 25/00* (2006.01)
*A61M 25/06* (2006.01)

(52) U.S. Cl.
CPC ......... *A61B 17/3478* (2013.01); *A61B 17/3421* (2013.01); *A61B 2017/22044* (2013.01); *A61M 25/0172* (2013.01); *A61M 25/09041* (2013.01); *A61M 2025/0004* (2013.01); *A61M 2025/0681* (2013.01); *A61M 2025/09125* (2013.01); *A61M 2025/09175* (2013.01)
USPC ............................ 606/108; 600/106; 600/585

(58) Field of Classification Search
CPC ............. A61M 2025/0681; A61M 2025/0004; A61M 2025/09125; A61M 25/0172
USPC .................................. 600/106, 184; 606/108
See application file for complete search history.

(56) References Cited

U.S. PATENT DOCUMENTS 5,059,183 A * 10/1991 Semrad ......................... 604/158
5,935,098 A * 8/1999 Blaisdell et al. .............. 604/515

(Continued)

OTHER PUBLICATIONS

Funaki et al., Percutaneous Nephrostomy, Semin Intervent Radiol 2006; 23:205-208.*

(Continued)

*Primary Examiner* — Anhtuan T Nguyen
*Assistant Examiner* — Rynae Boler
(74) *Attorney, Agent, or Firm* — Neil D. Gershon

(57) ABSTRACT

A method for creating a tract in retrograde fashion for nephrostomy tube creation comprising the steps of providing a puncture wire having a tissue penetrating tip shielded in a sheath, inserting the puncture wire and sheath through a channel in an ureteroscope, advancing the puncture wire from the sheath while visualizing under direct vision a position of the puncture wire, advancing the puncture wire through a selected calyx, and inserting antegrade a coaxial catheter over the puncture wire.

9 Claims, 30 Drawing Sheets

(56) References Cited

U.S. PATENT DOCUMENTS

| 7,713,193 | B2 | 5/2010 | Nance et al. | |
|---|---|---|---|---|
| 2007/0005019 | A1* | 1/2007 | Okishige | 604/175 |
| 2008/0255424 | A1* | 10/2008 | Durgin et al. | 600/156 |
| 2009/0187147 | A1* | 7/2009 | Kurth et al. | 604/161 |
| 2012/0041422 | A1 | 2/2012 | Whiting et al. | |

OTHER PUBLICATIONS

Munch, Direct-Vision Modified Lawson Retrograde Nephrostomy Technique Using Flexible Ureteroscope, Journal of Endourology 1989; 3(4):411-417.*

Hosking, Retrograde Access, Smith's Textbook of Endourology 2007, pp. 117-121.*

Lawson Retrograde Nephrostomy Wire Puncture Set, Cook Medical, Cook Urological, Inc., 1984.

Anatomical Relationship Between the Intrarenal Arteries and the Kidney Collecting System, The Journal of Urology, vol. 143, Apr. 1990.

X-ray-free Percutaneous Nephrolithotomy in Supine Position With Ultrasound Guidance, © Springer-Verlag 2009.

Factors Affecting Patient Radiation Exposure During Percutaneous Nephrolithotomy, Duke University Medical Center, Durham, North Carolina, The Journal of Urology, Dec. 2010.

A Novel 5-Part Percutaneous Access Needle With Glidewire Technique (5-PANG) for Percutaneous Nephrolithotomy: Our Initial Experience, Surgeon's Workshop, Ashish V. Patil, 2009.

Smith's Textbook of Endourology, Second Edition, 2007 BC Decker Inc.

Endoscopy-Guided Percutaneous Nephrostolithotomy: Benefits of Ureteroscopic Access and Therapy, Journal of Endourology, vol. 23, No. 10, Oct. 2009.

Direct-Vision Modified Lawson Retrograde Nephrostomy Technique Using Flexible Ureteroscope, Larry C. Munch, M.D., Journal of Endourology, vol. 3, No. 4, 1989.

A Method for Teaching Junior Urologists How to Gain Access to the Pelvicalyceal System Under Fluoroscopy, © 2010 UroToday International Journal, vol. 3, Issue 4, August.

Determining Site of Skin Puncture for Percutaneous Renal Access Using Fluoroscopy-Guided Triangulation Technique, Tricks of the Trade, Journal of Endourology, vol. 3, No. 2, Feb. 2009.

Lower-Pole Fluoroscopy-Guided Percutaneous Renal Access: Which Calix is Posterior?, Brian H. Eisner, M.D., Jordan Cloyd, B.A. and Marshall L. Stoller, M.D., Journal of Endourology, vol. 23, No. 10, Oct. 2009.

Ureteroscopy Assisted Retrograde Nephrostomy: A New Technique for Percutaneous Nephrolithotomy (PCNL), Dec. 5, 2011.

* cited by examiner

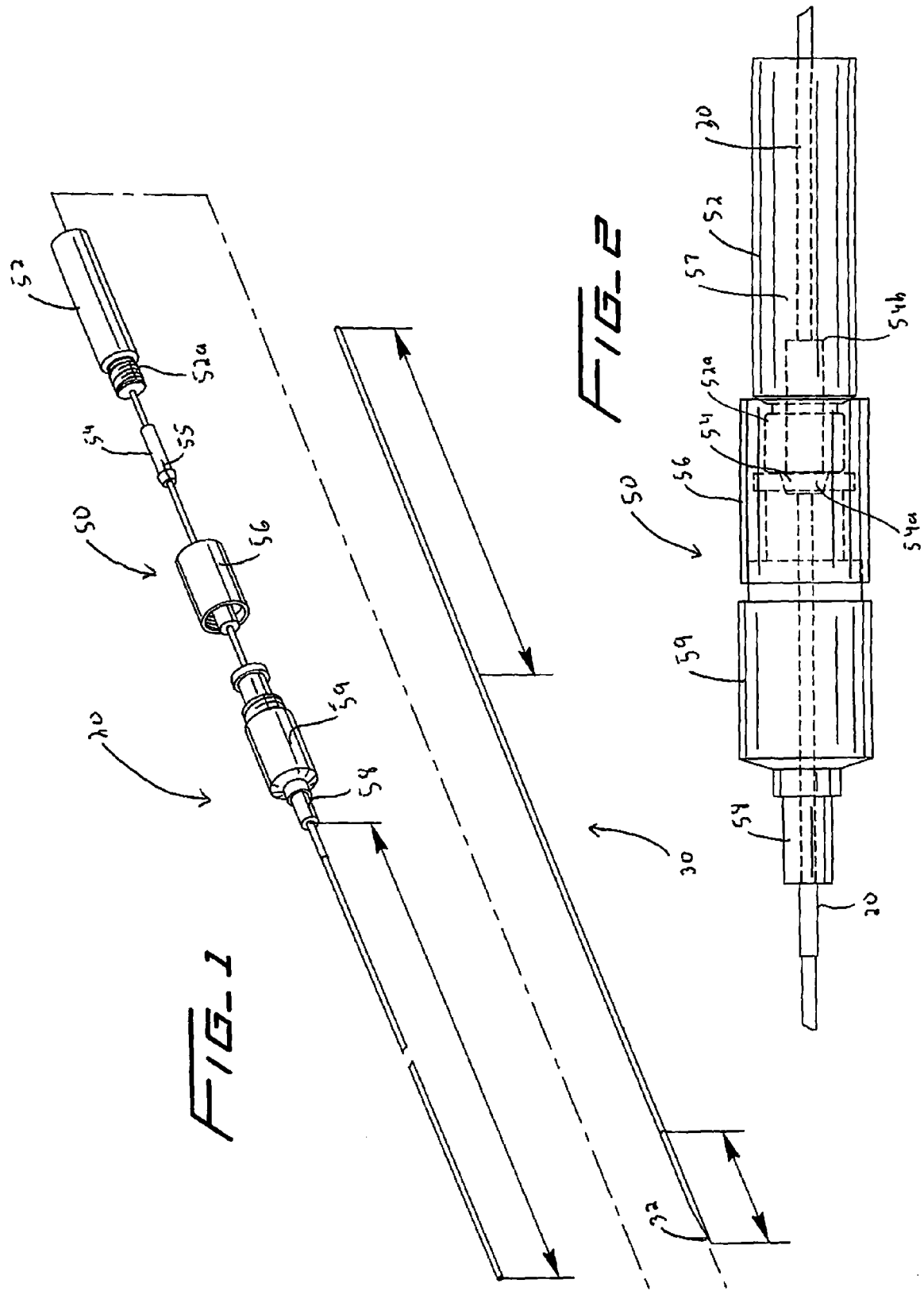

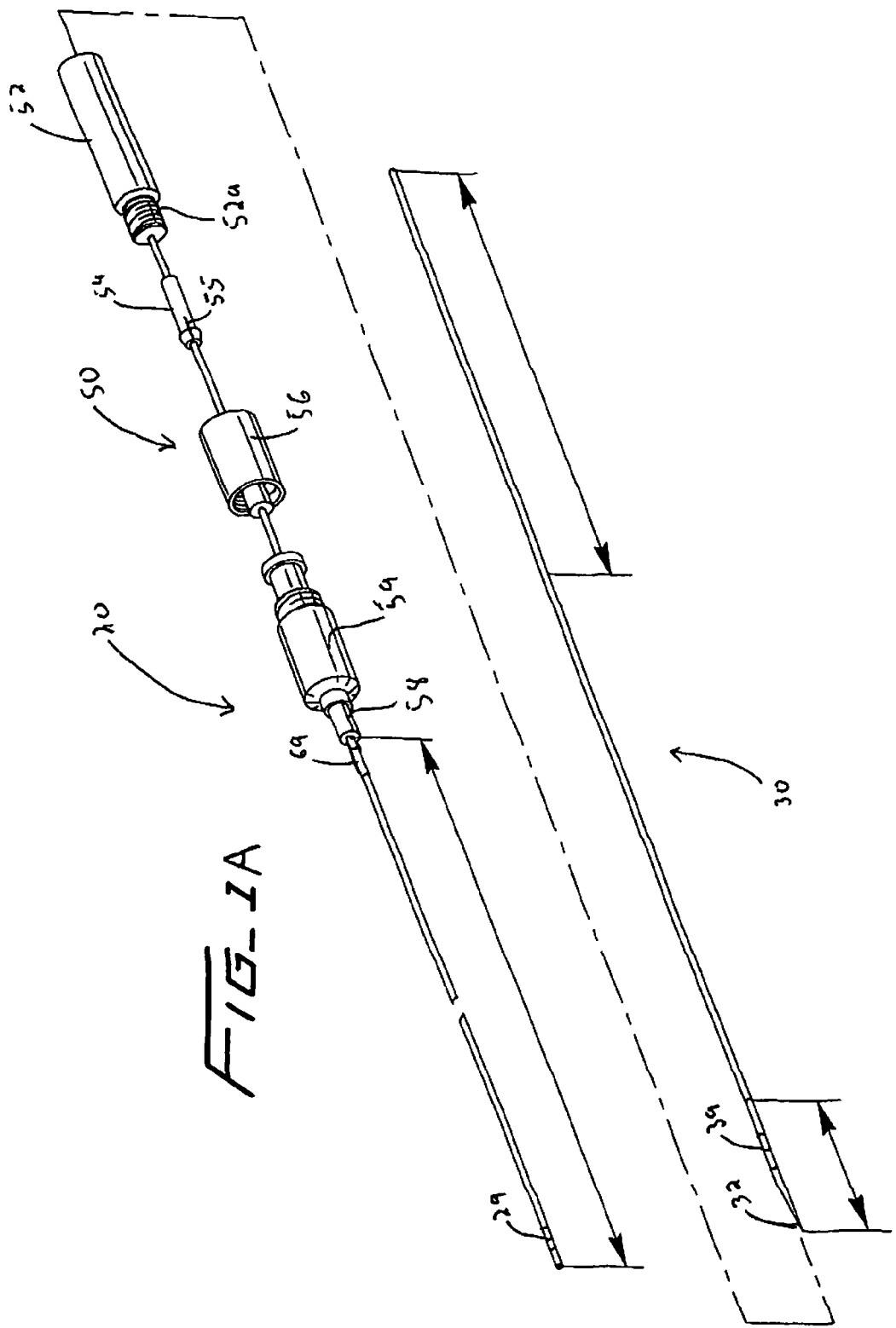
FIG_1A

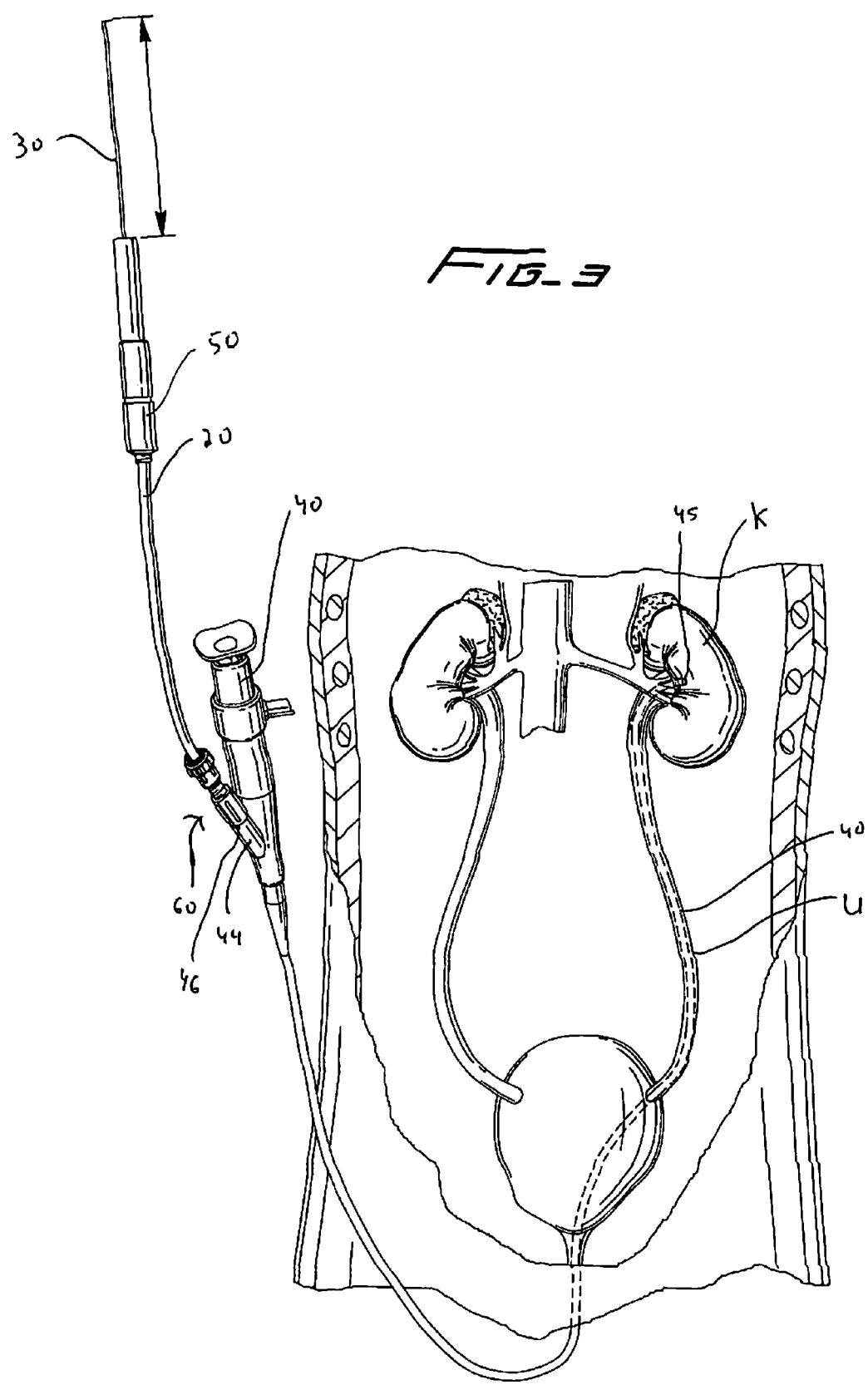

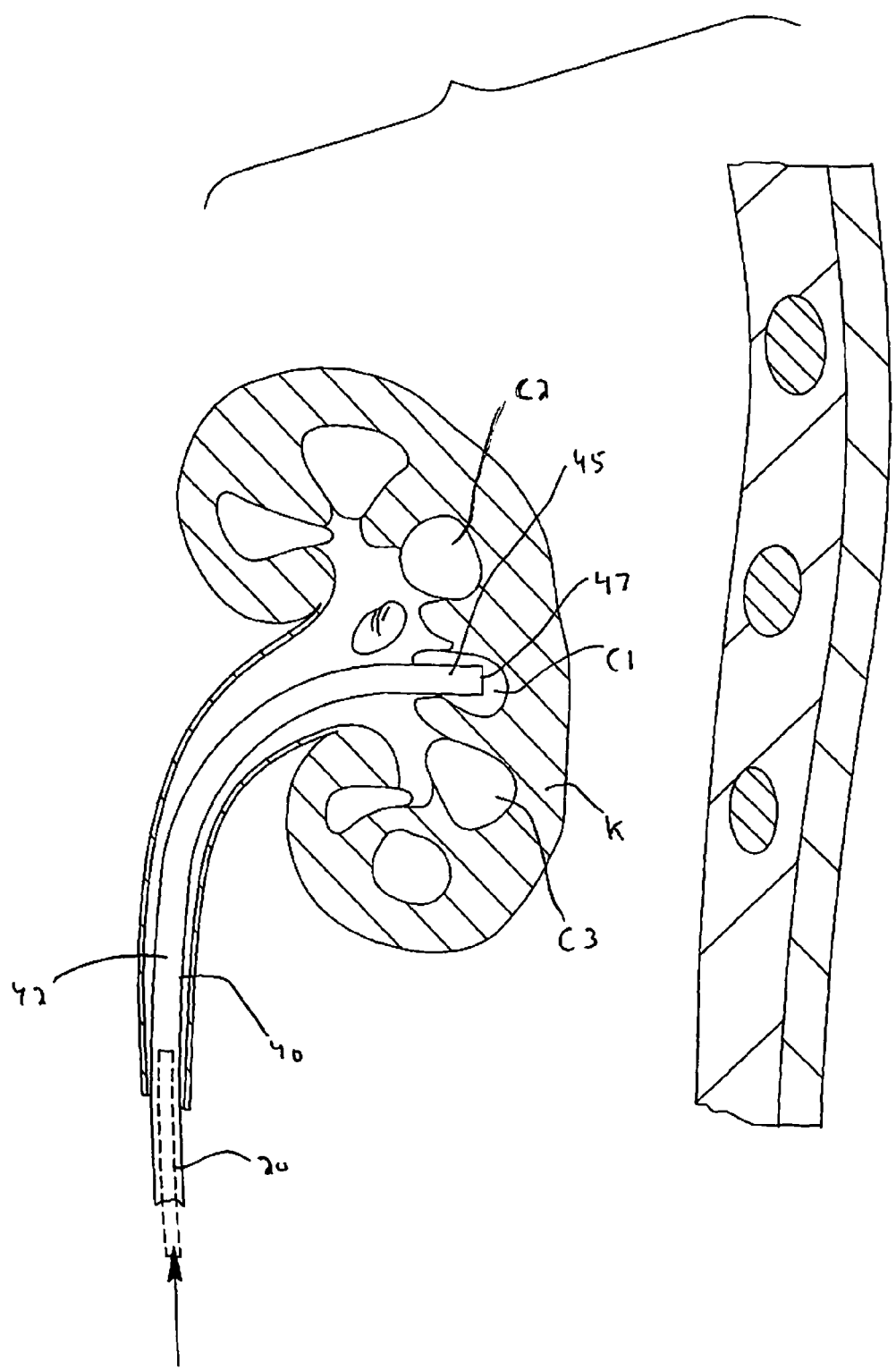

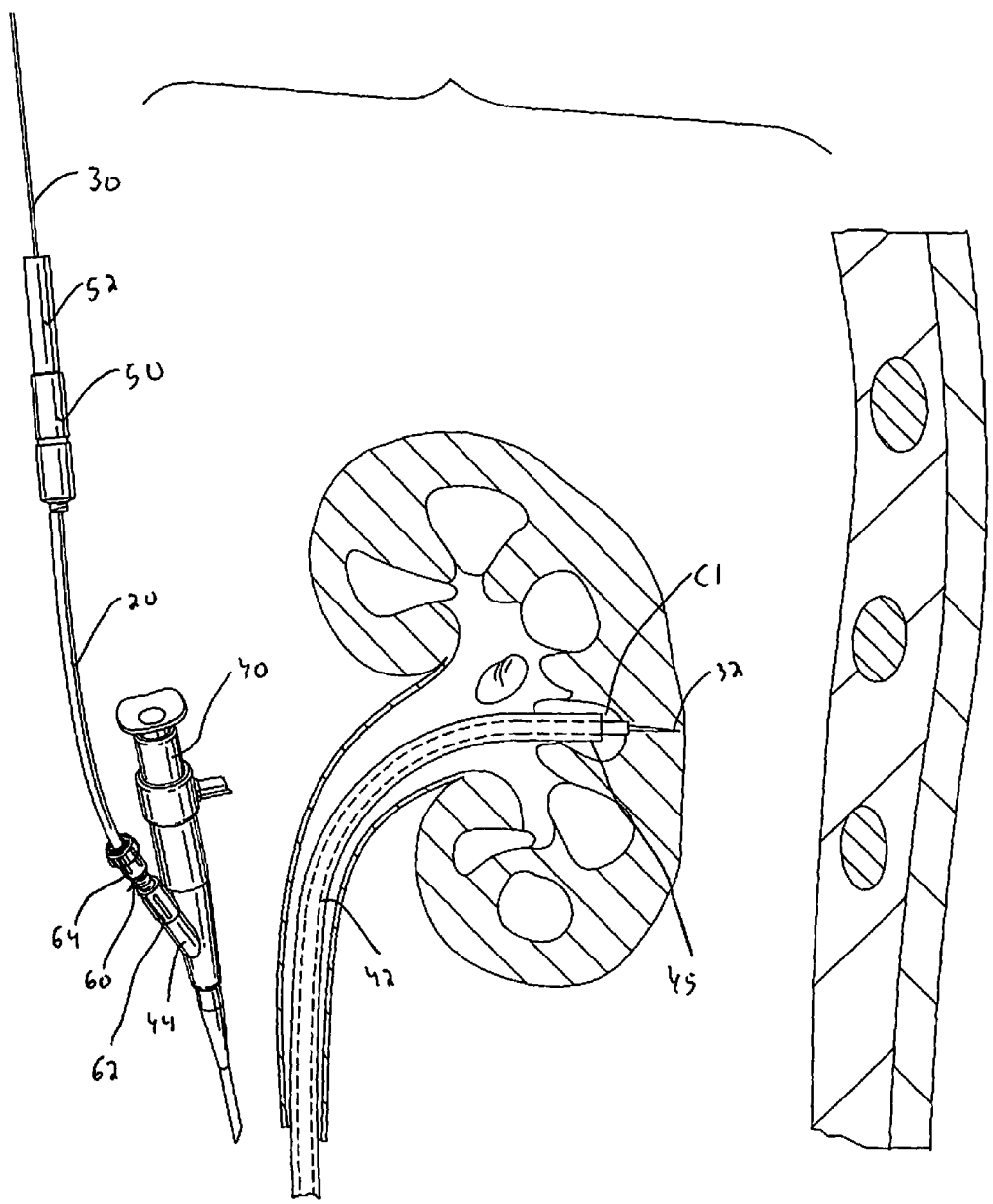

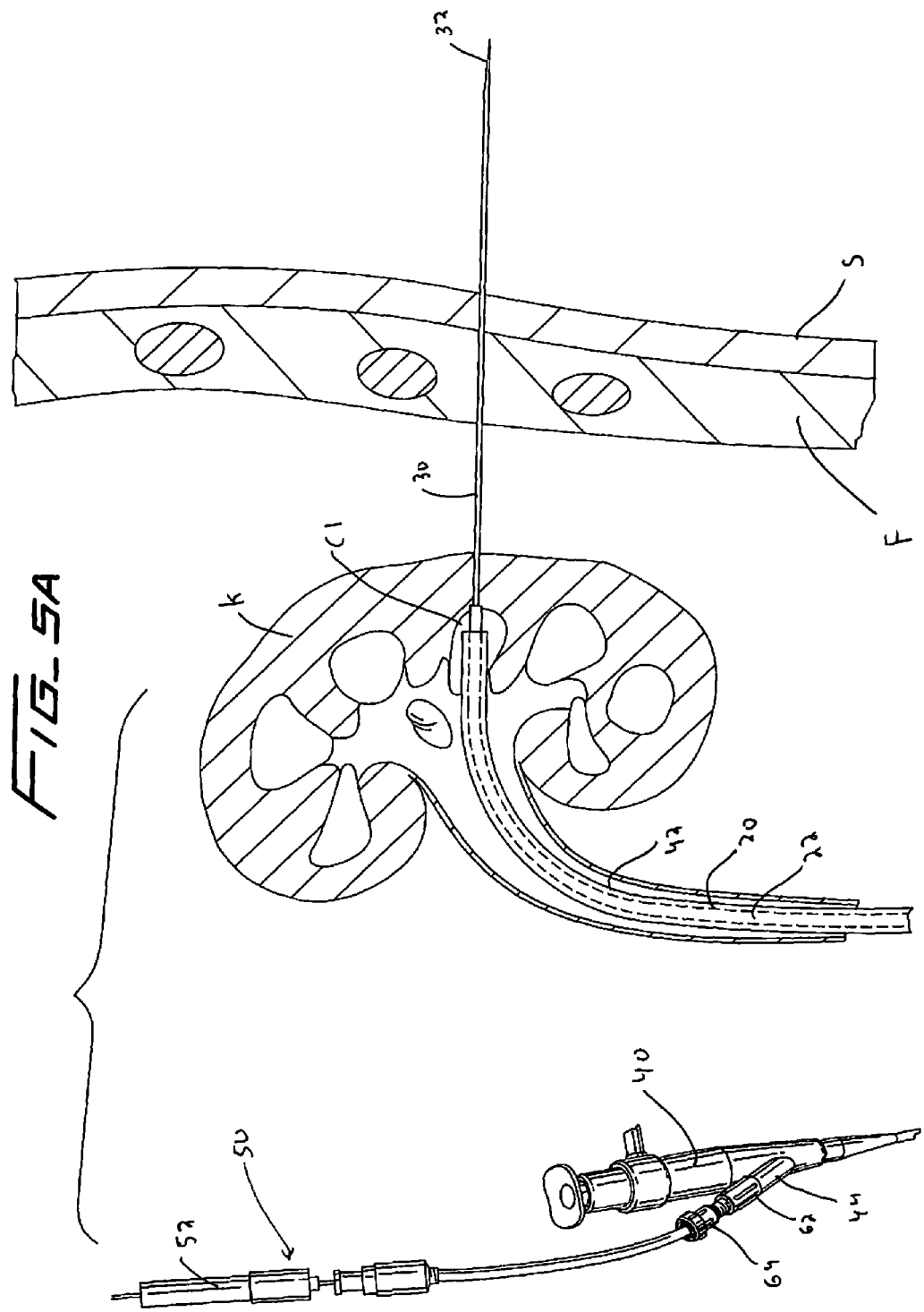

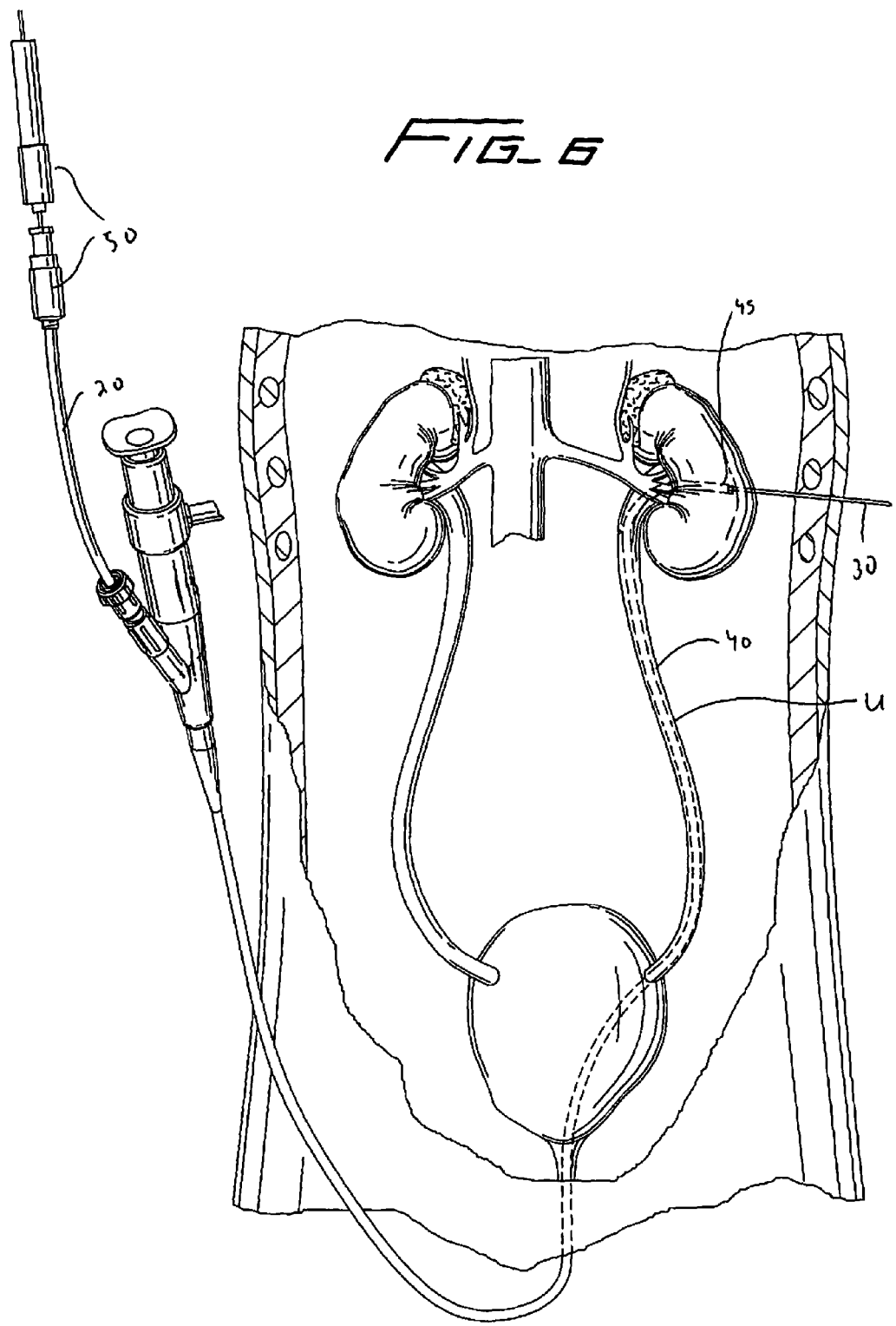
FIG_6

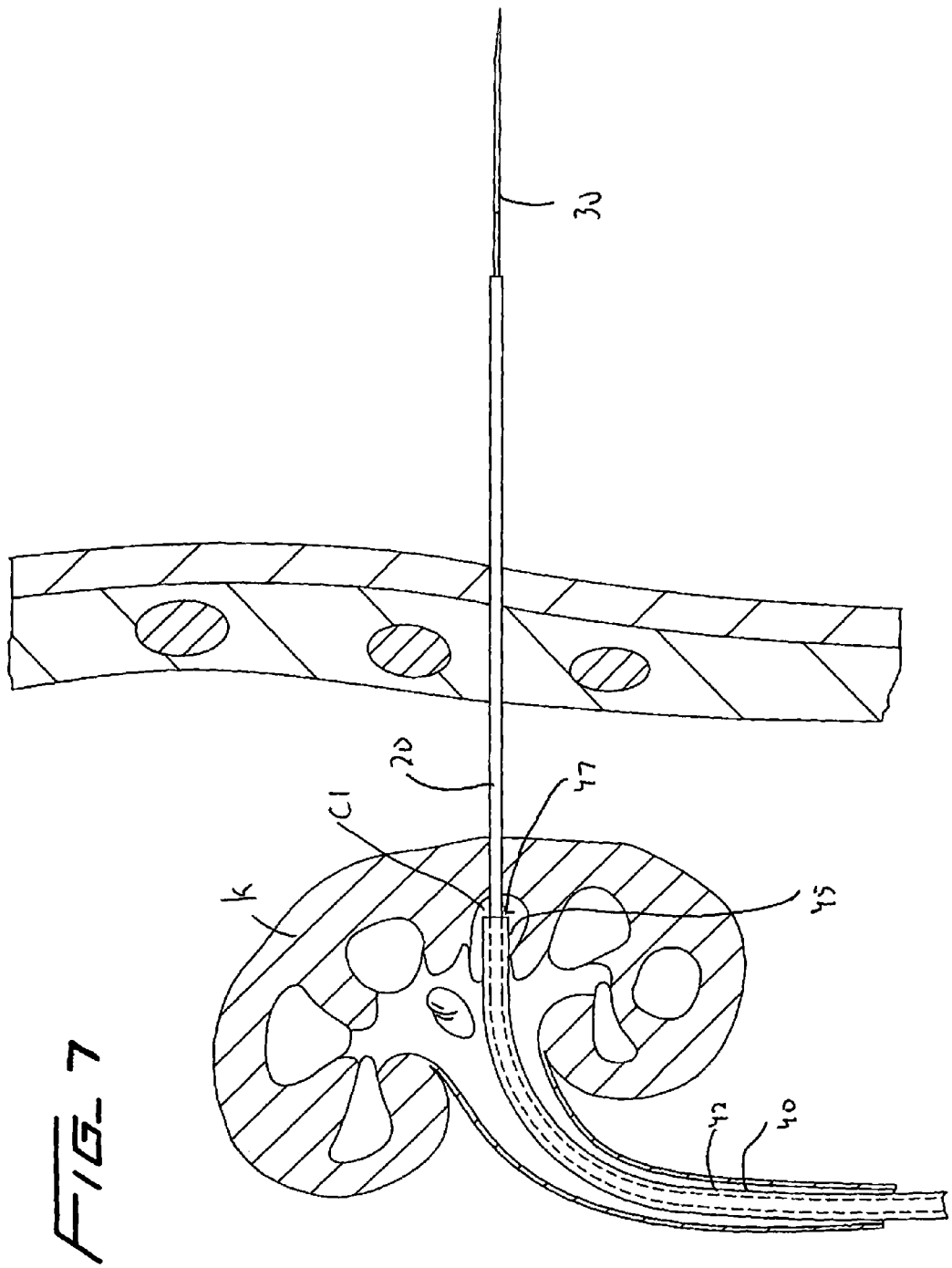

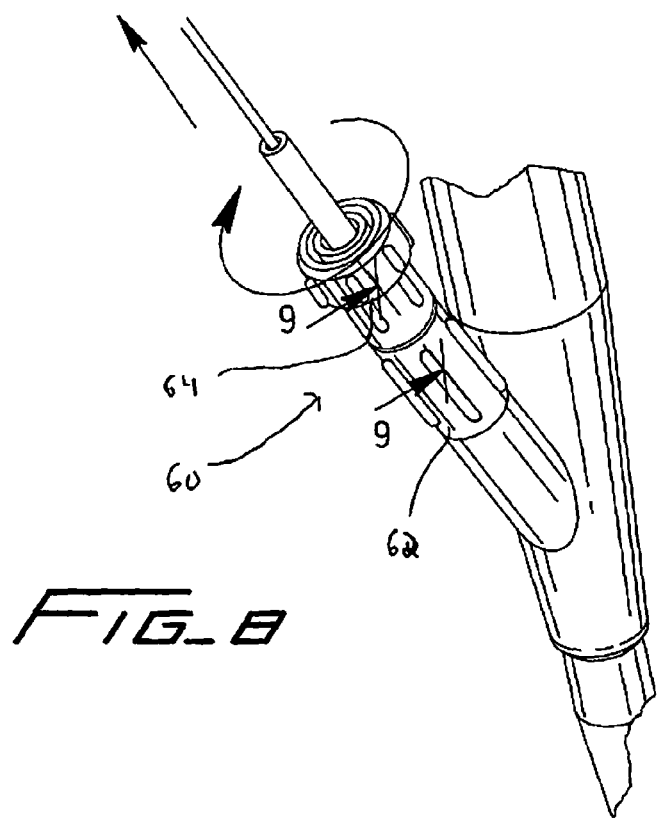
FIG_8
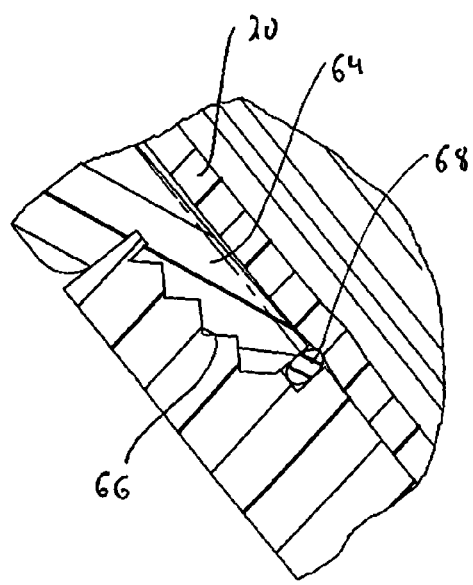
FIG_9

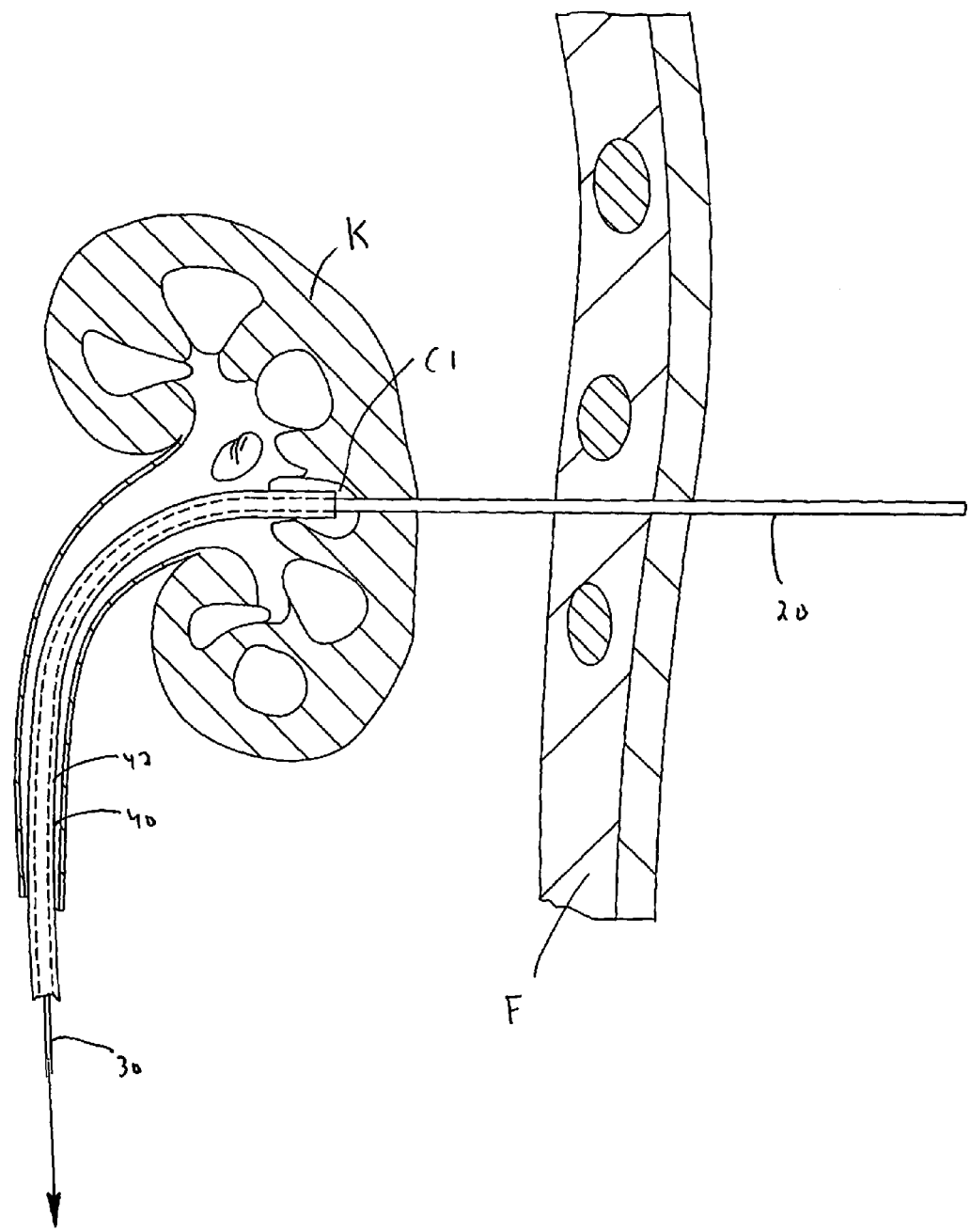

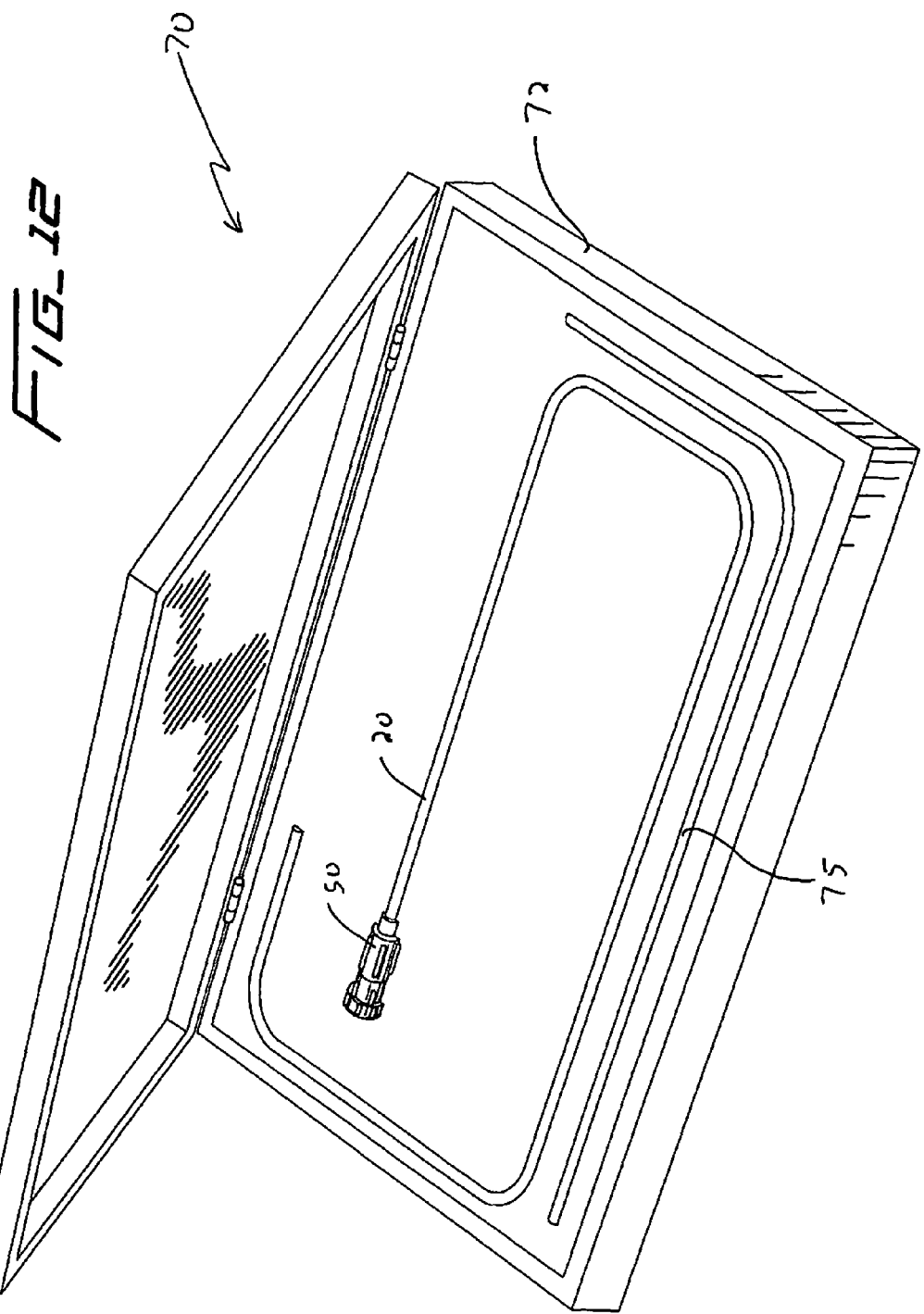

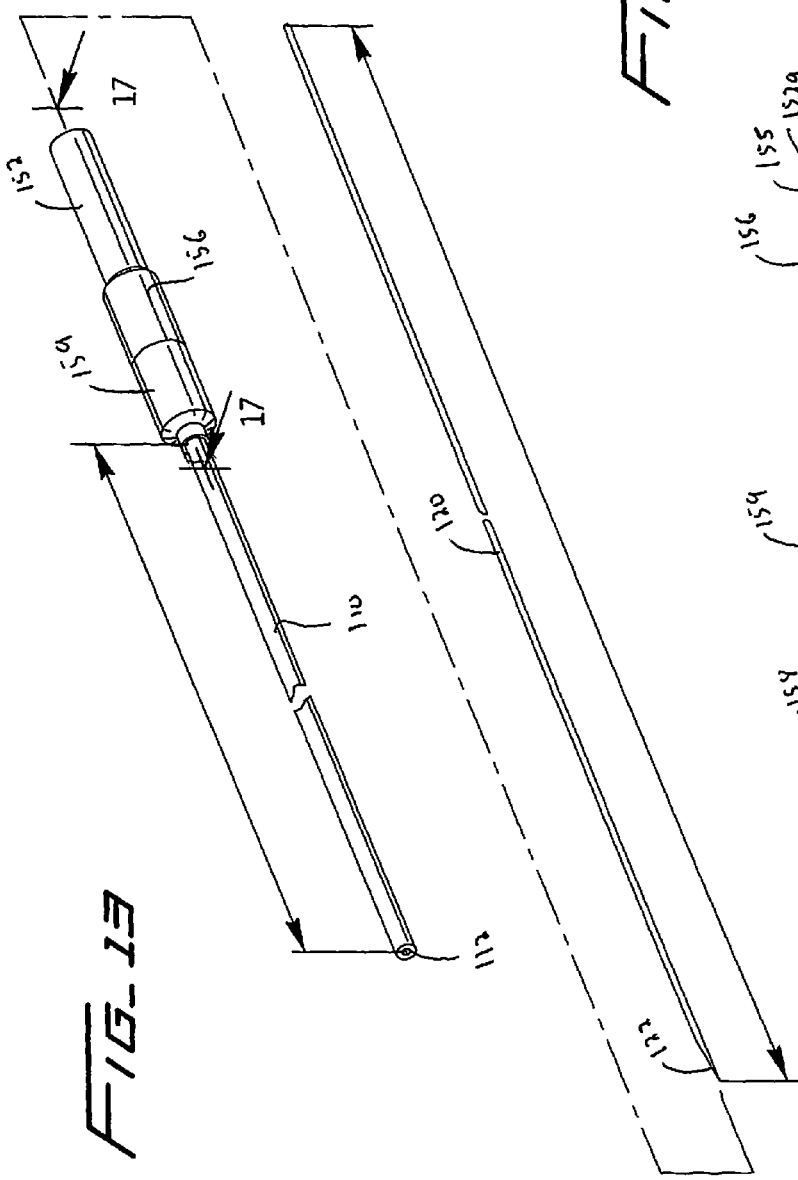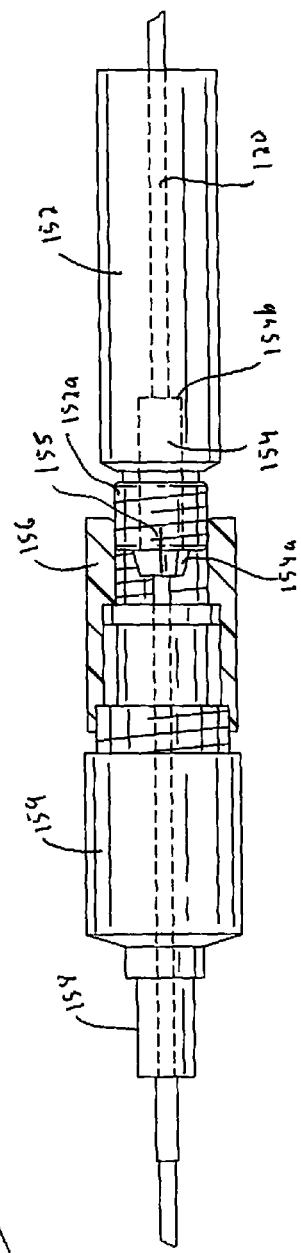

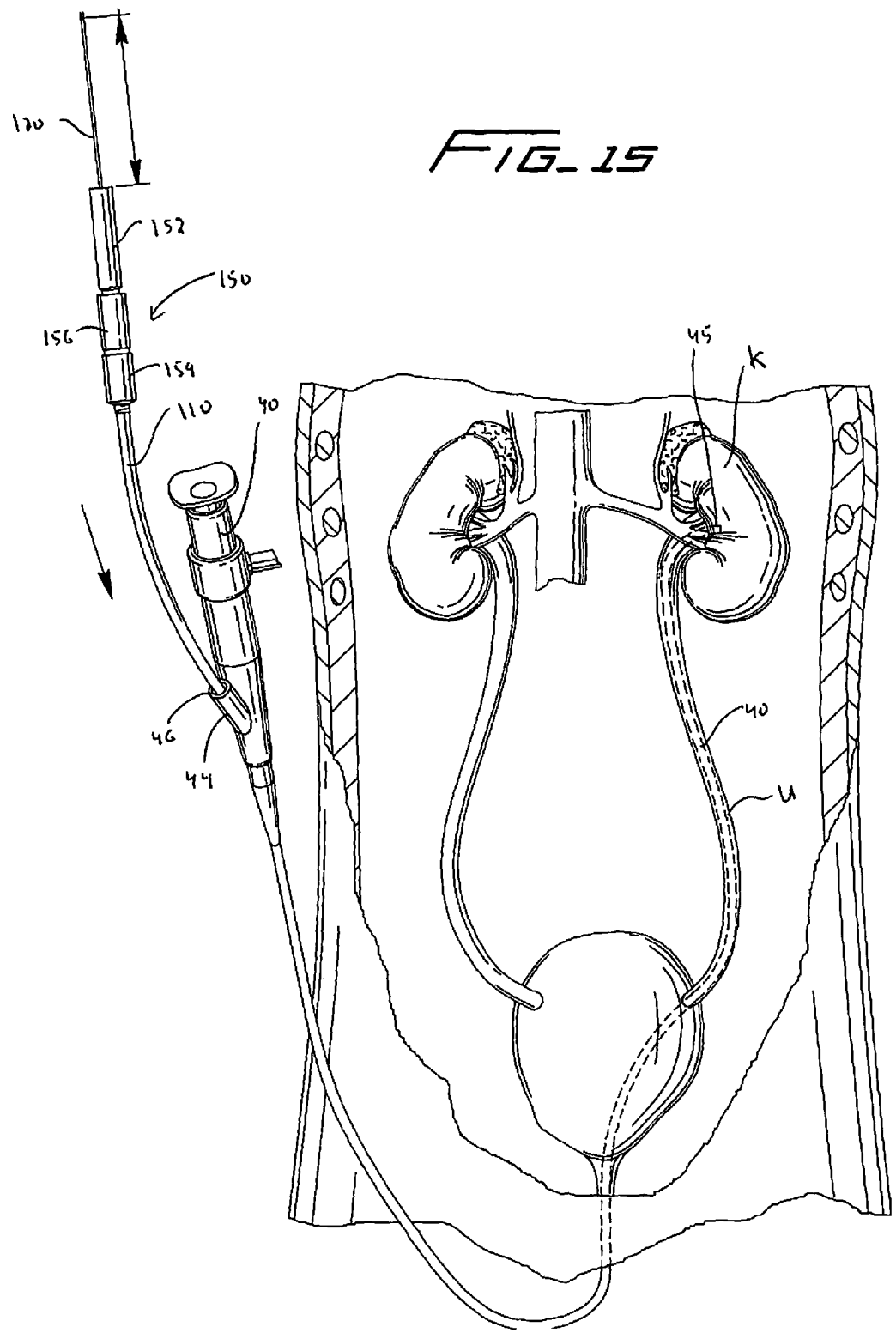
FIG_15

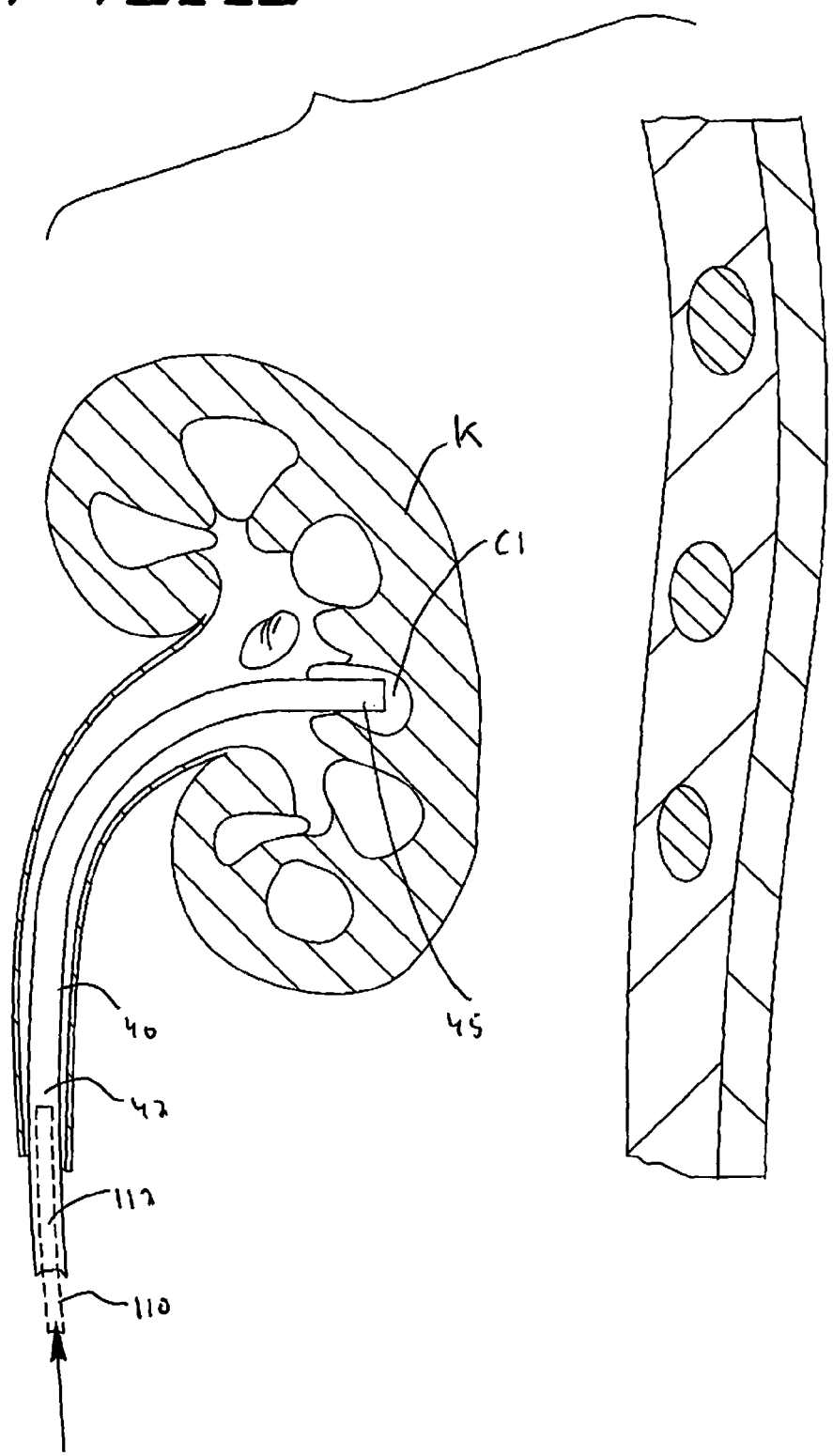
FIG_16

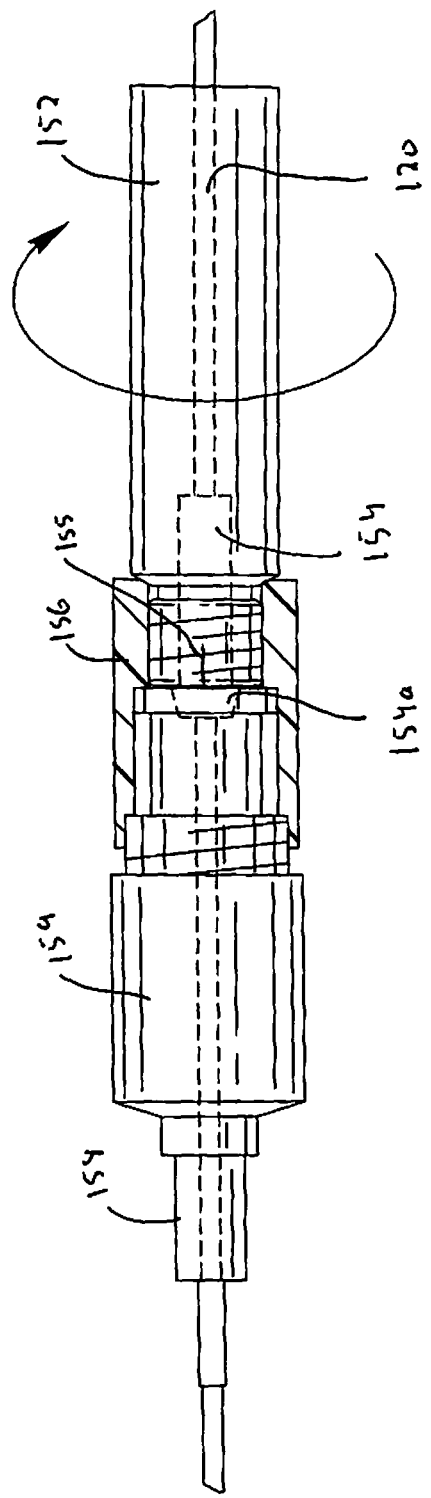

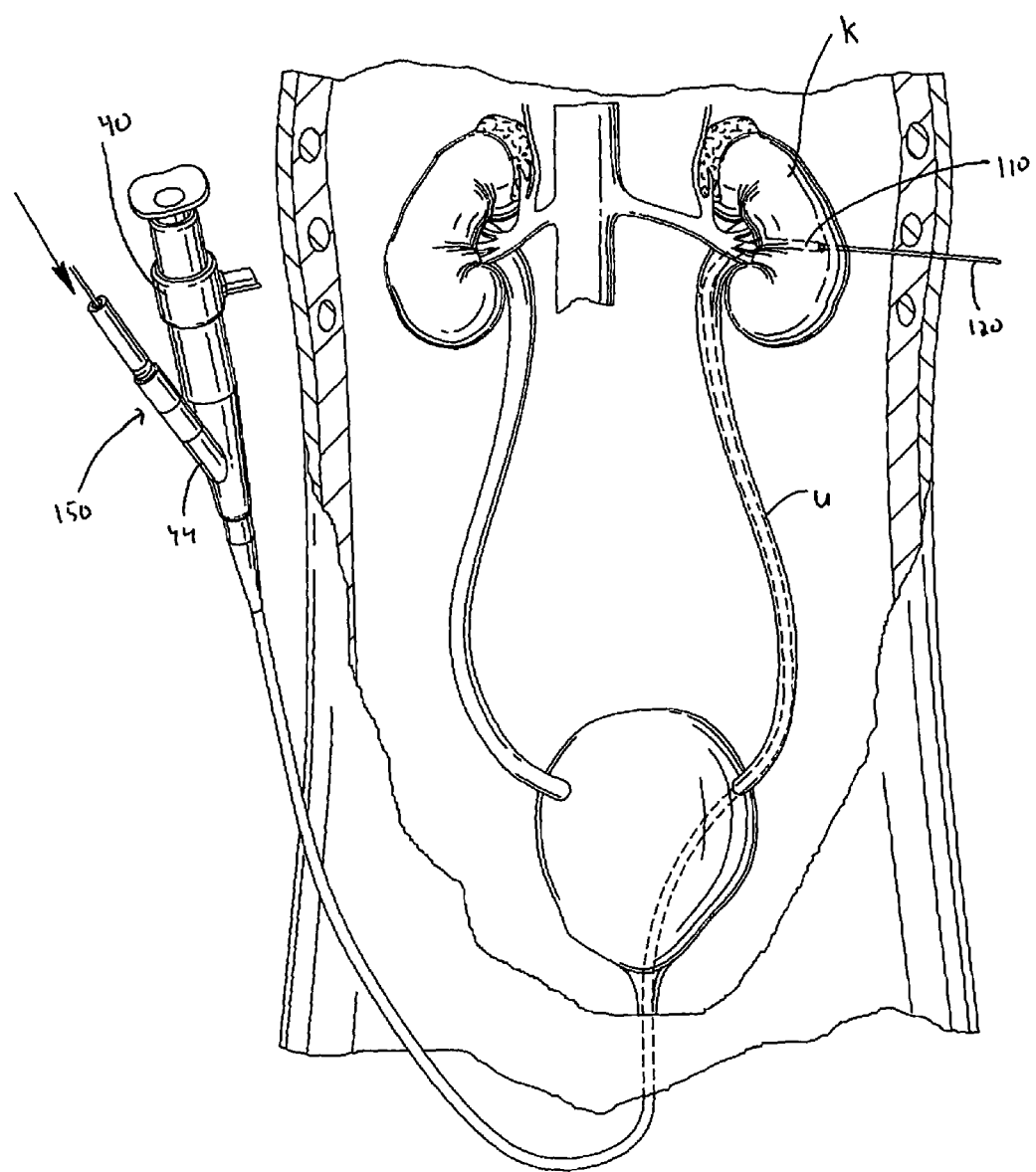

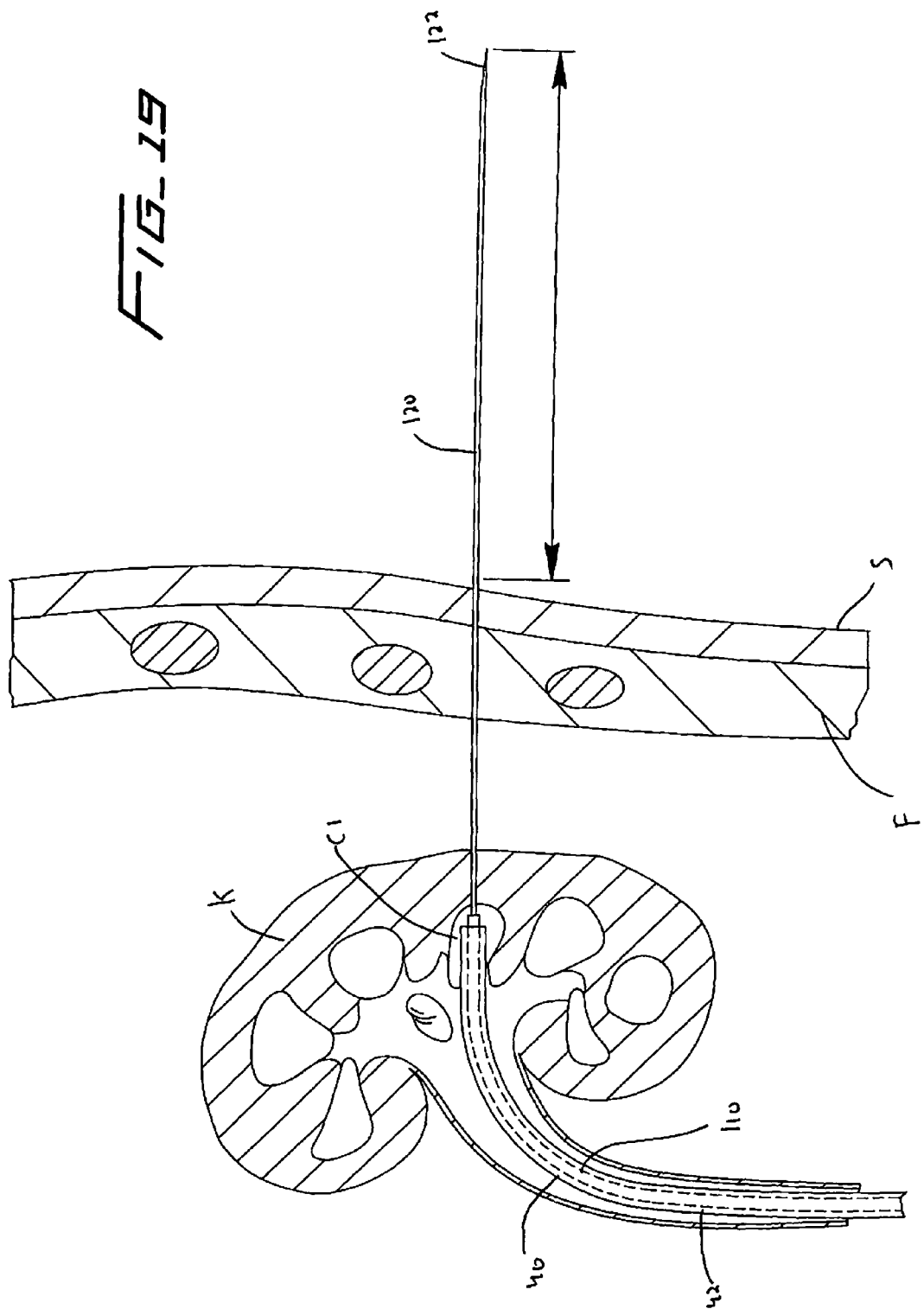

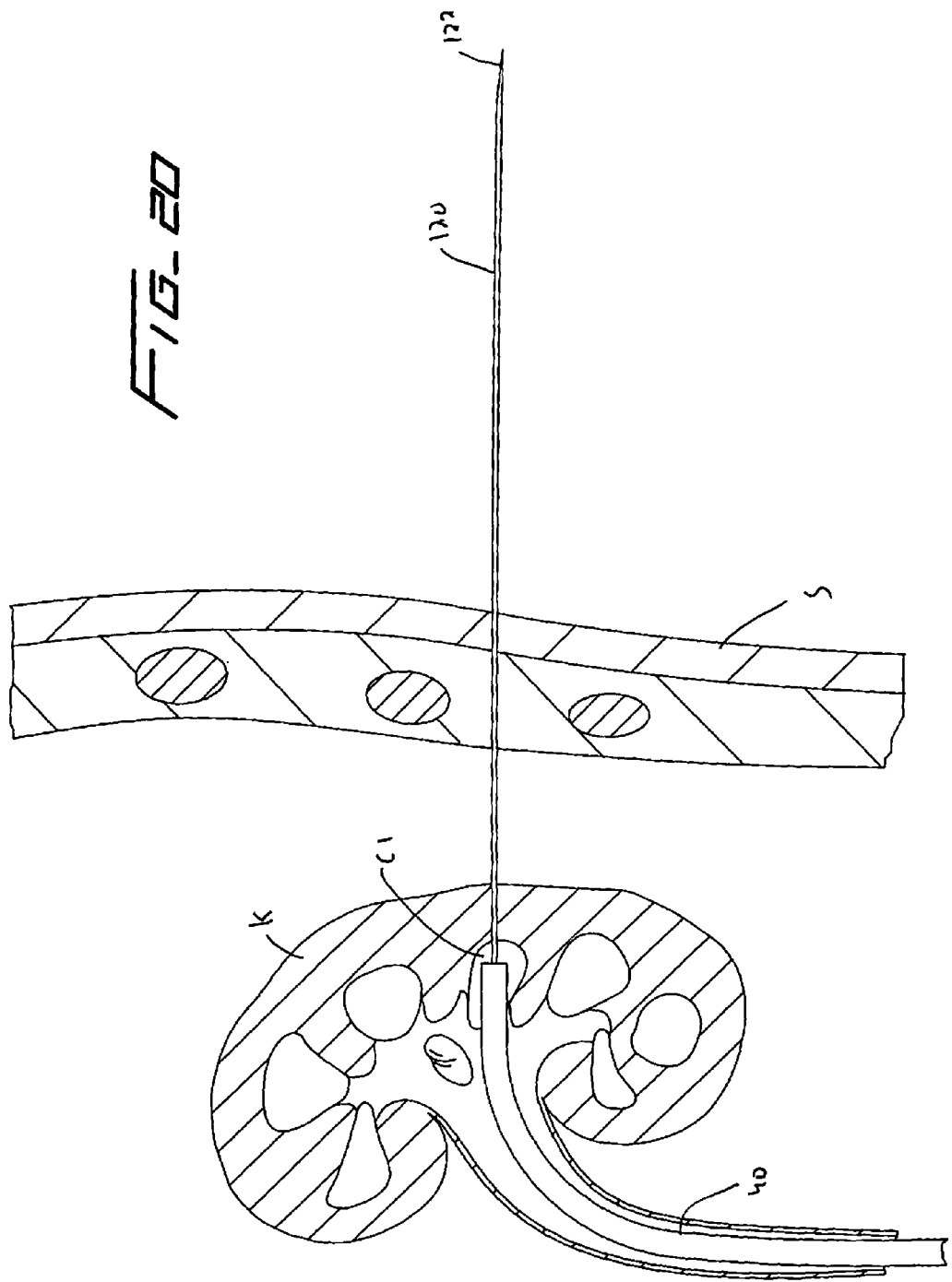

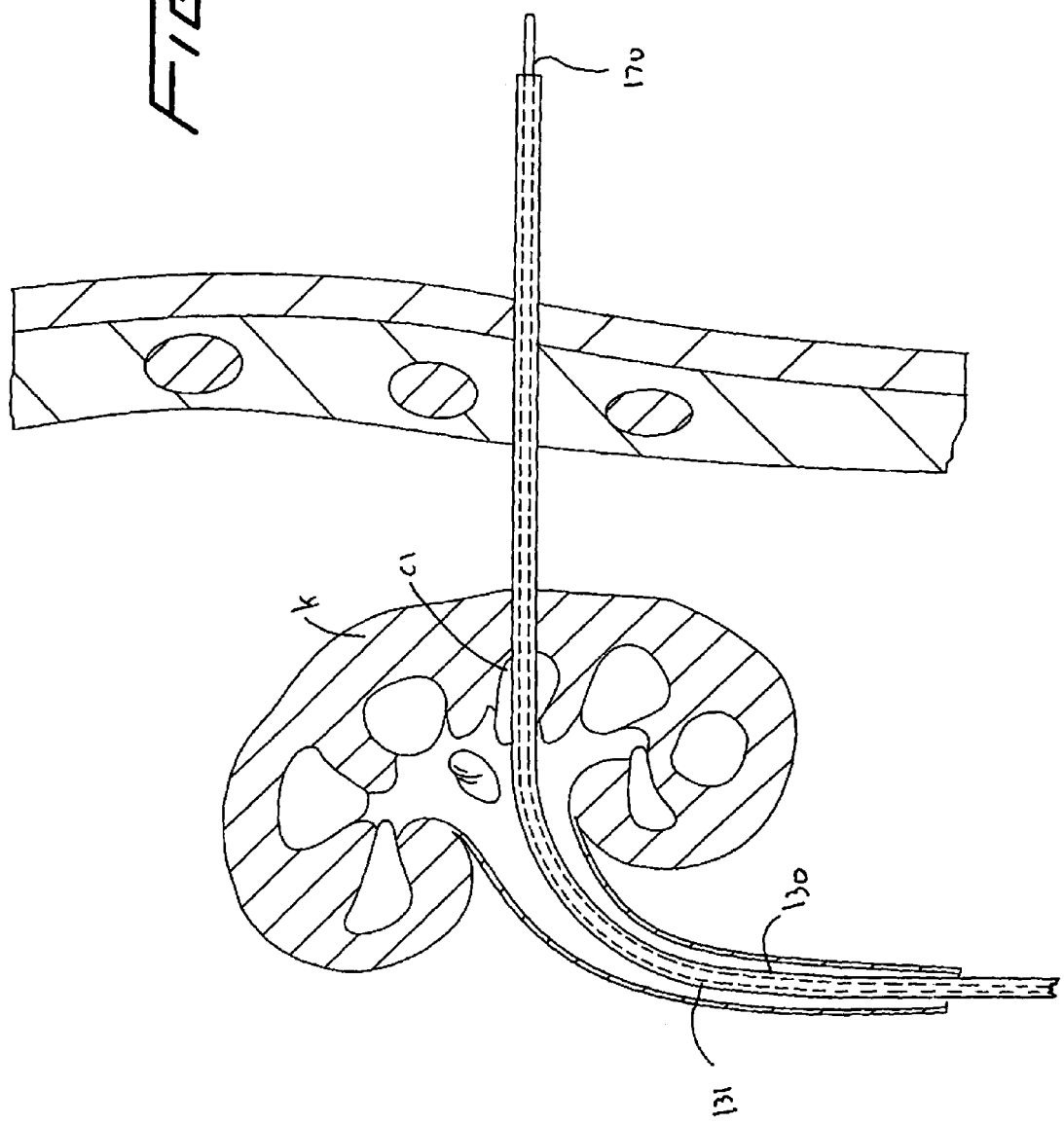

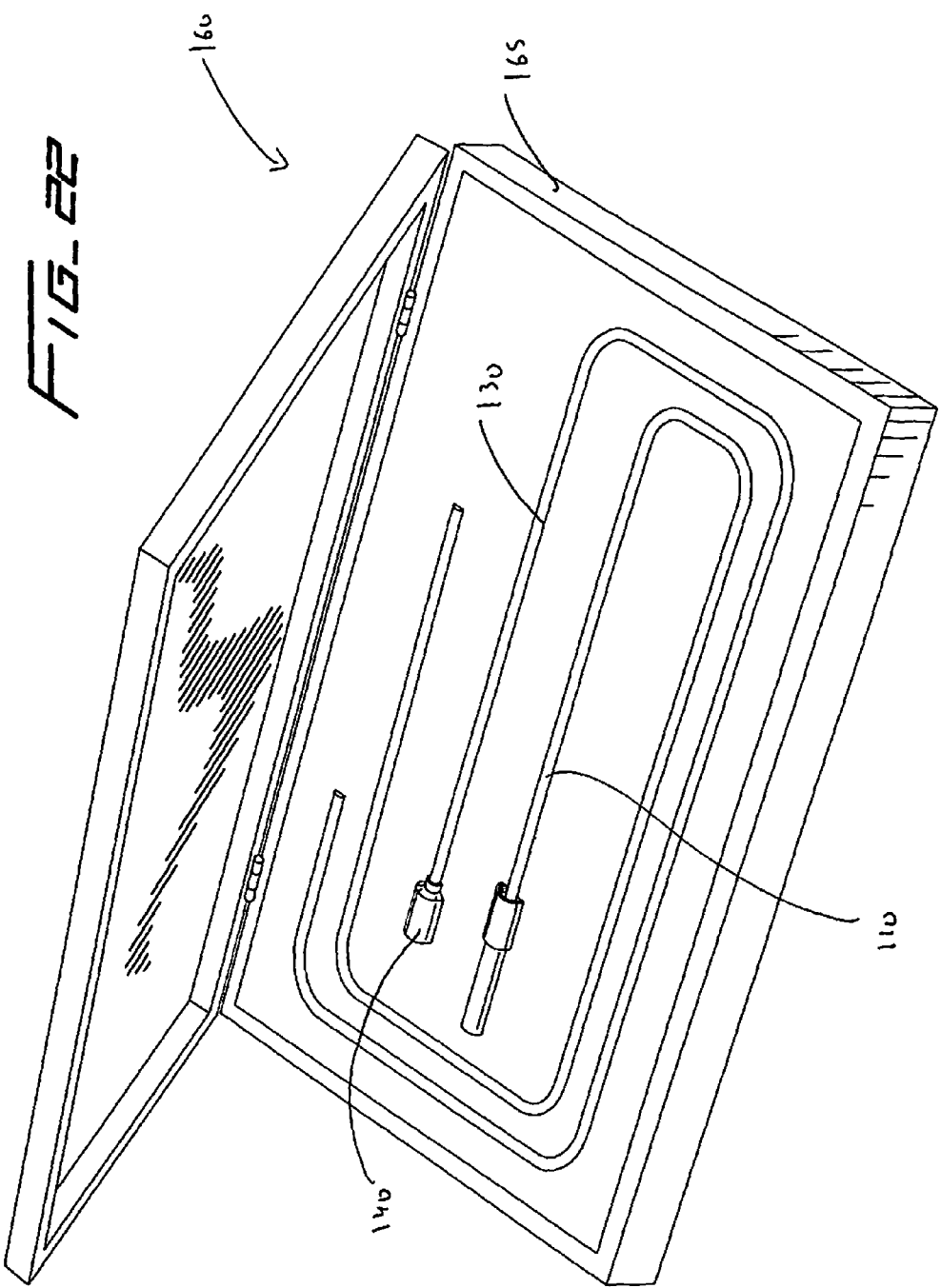

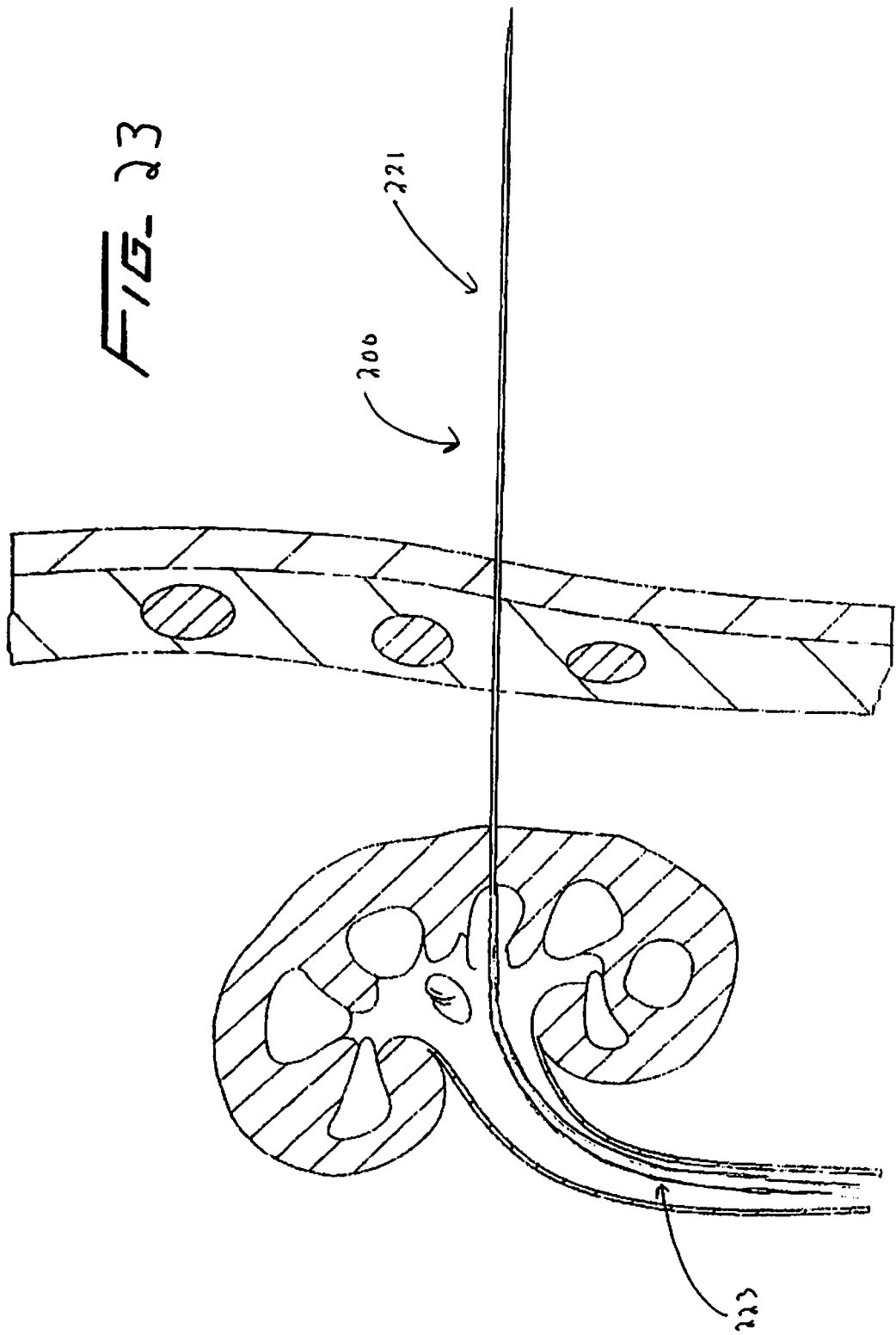

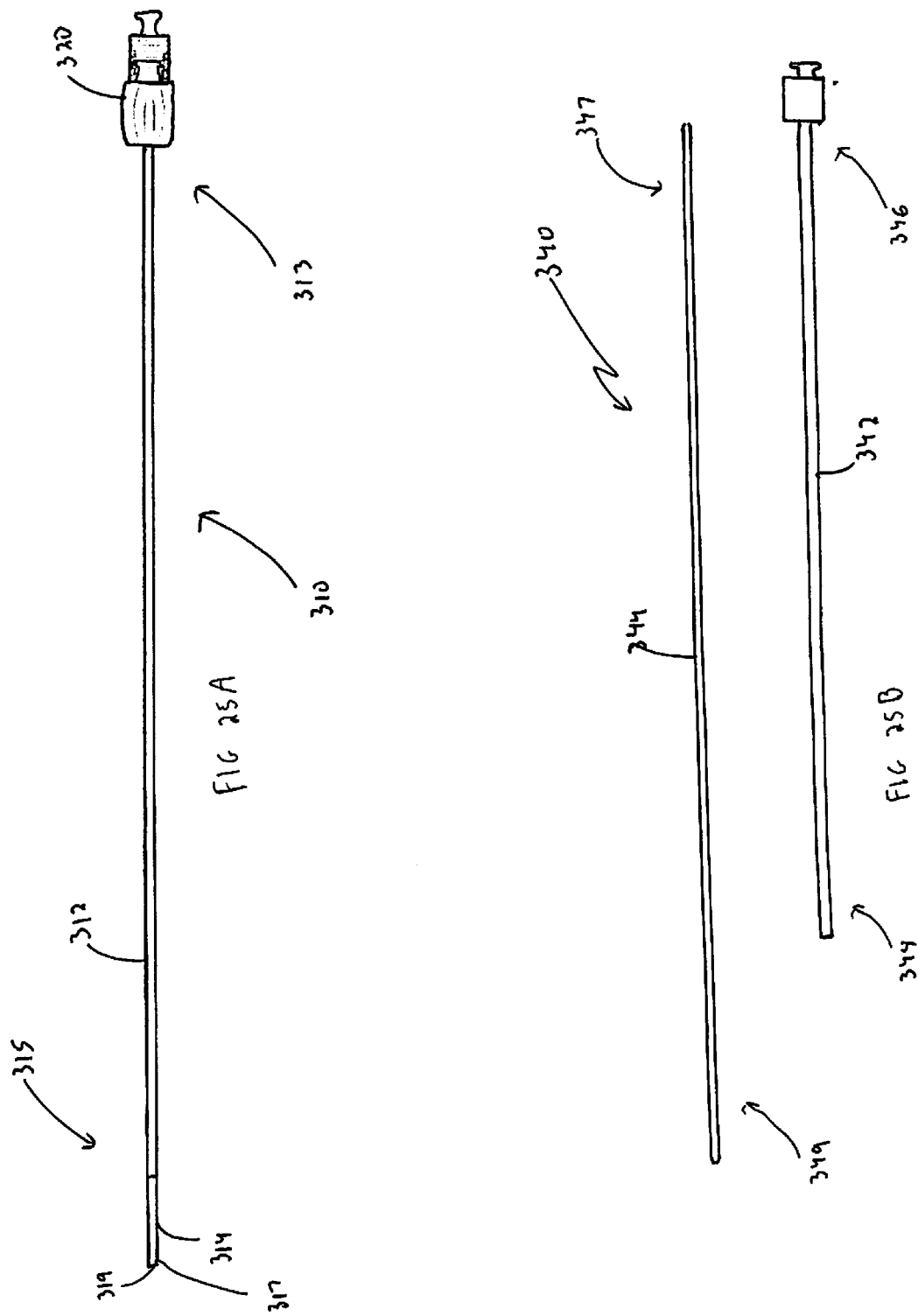

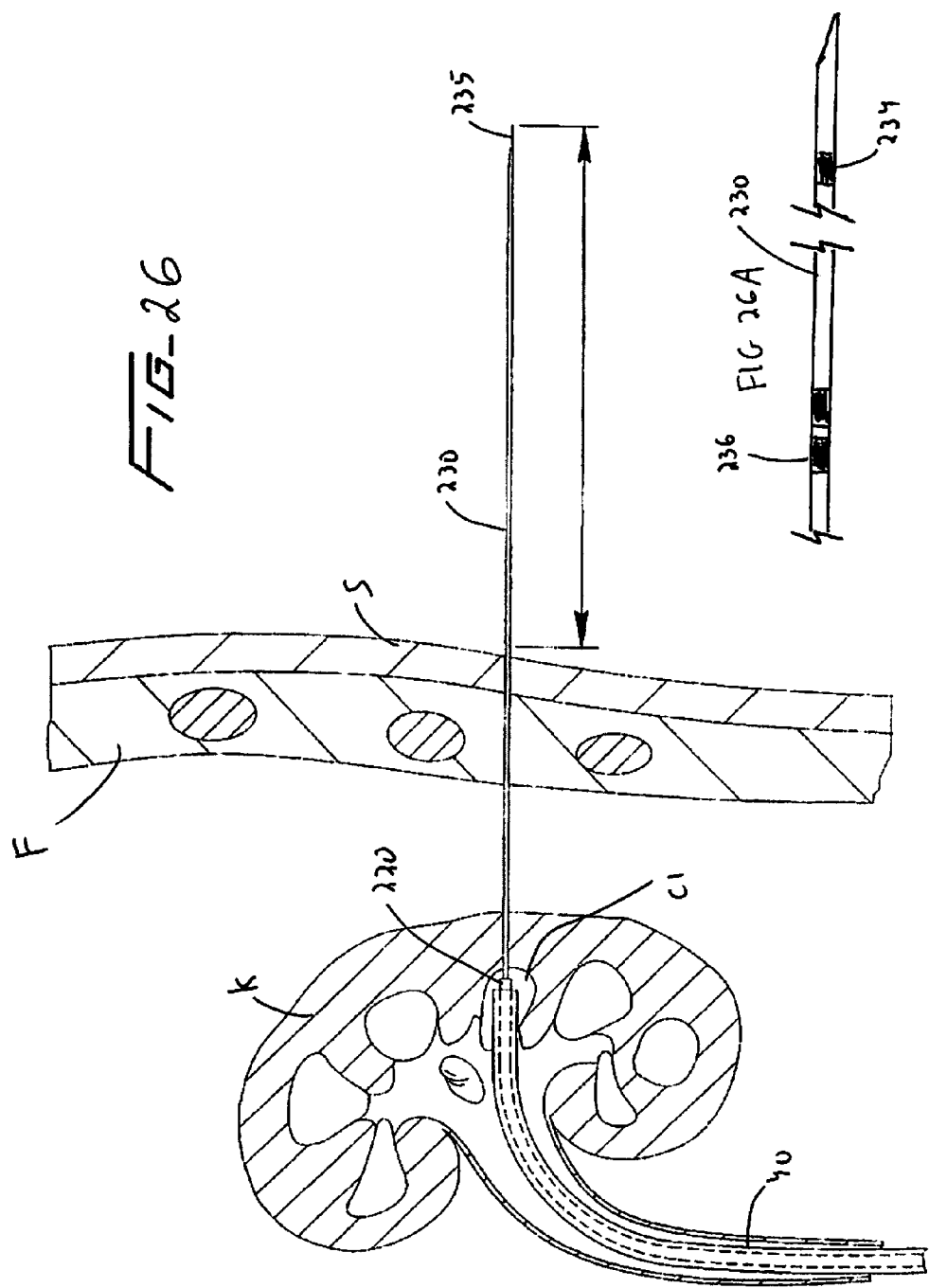

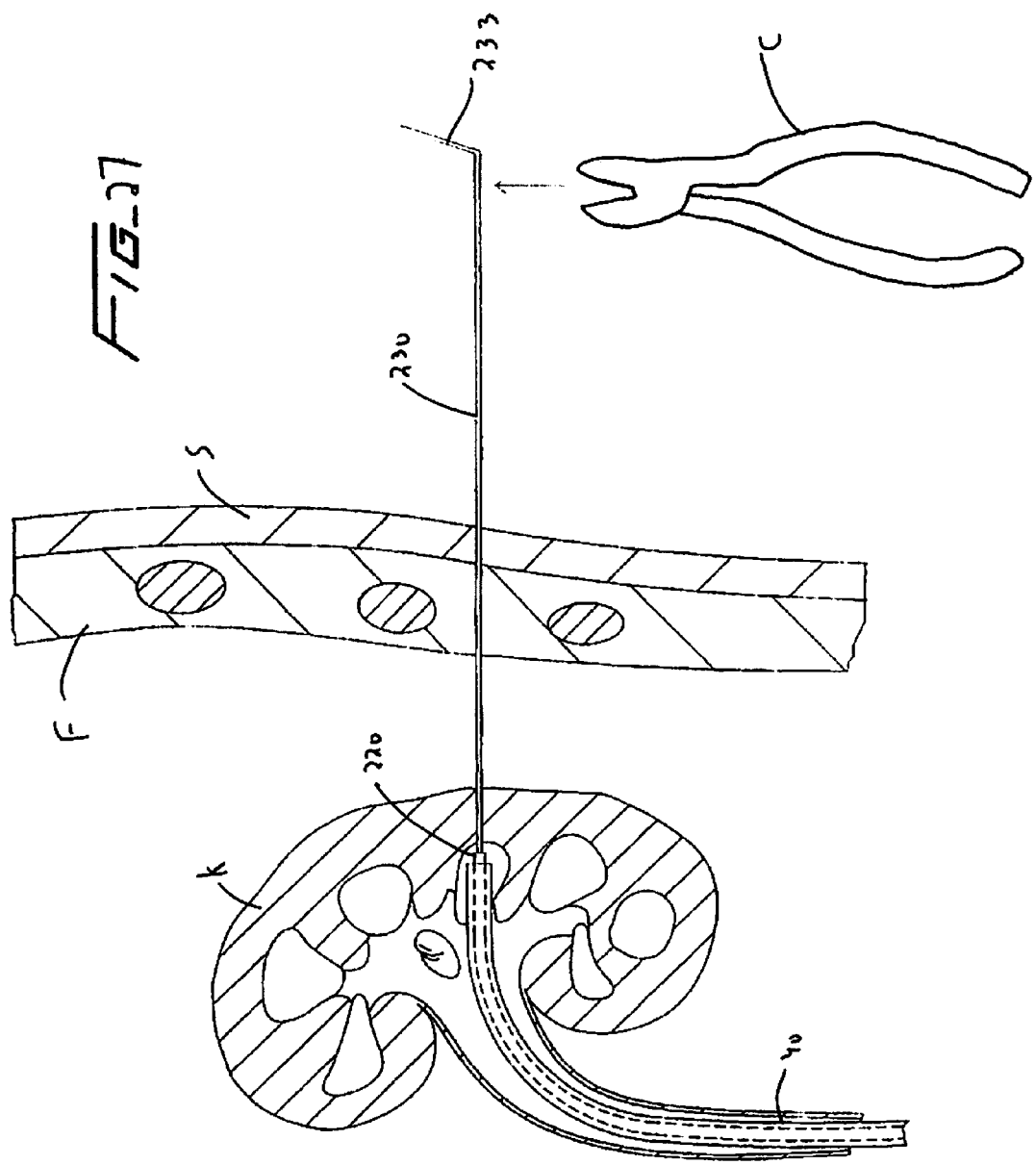

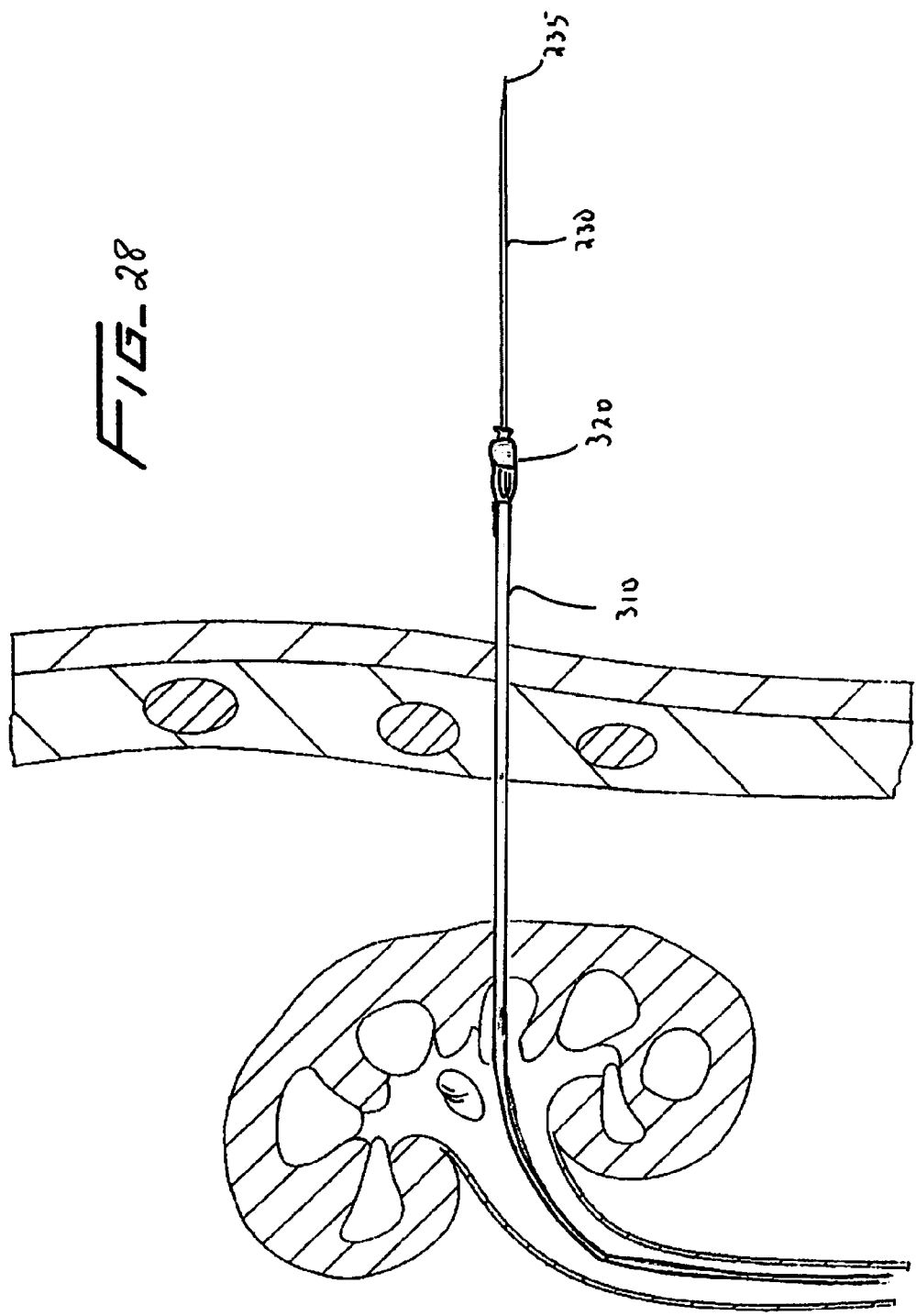

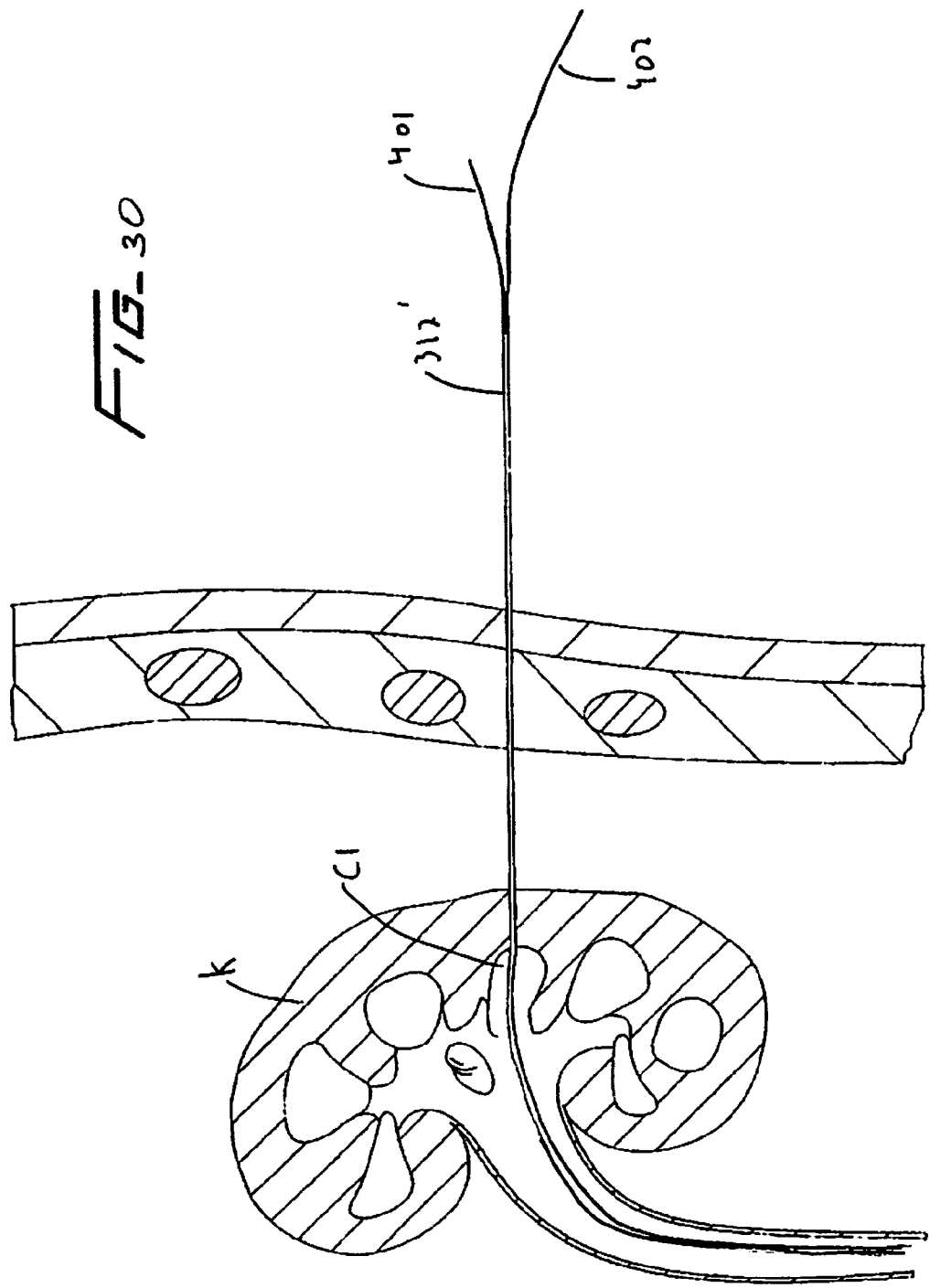

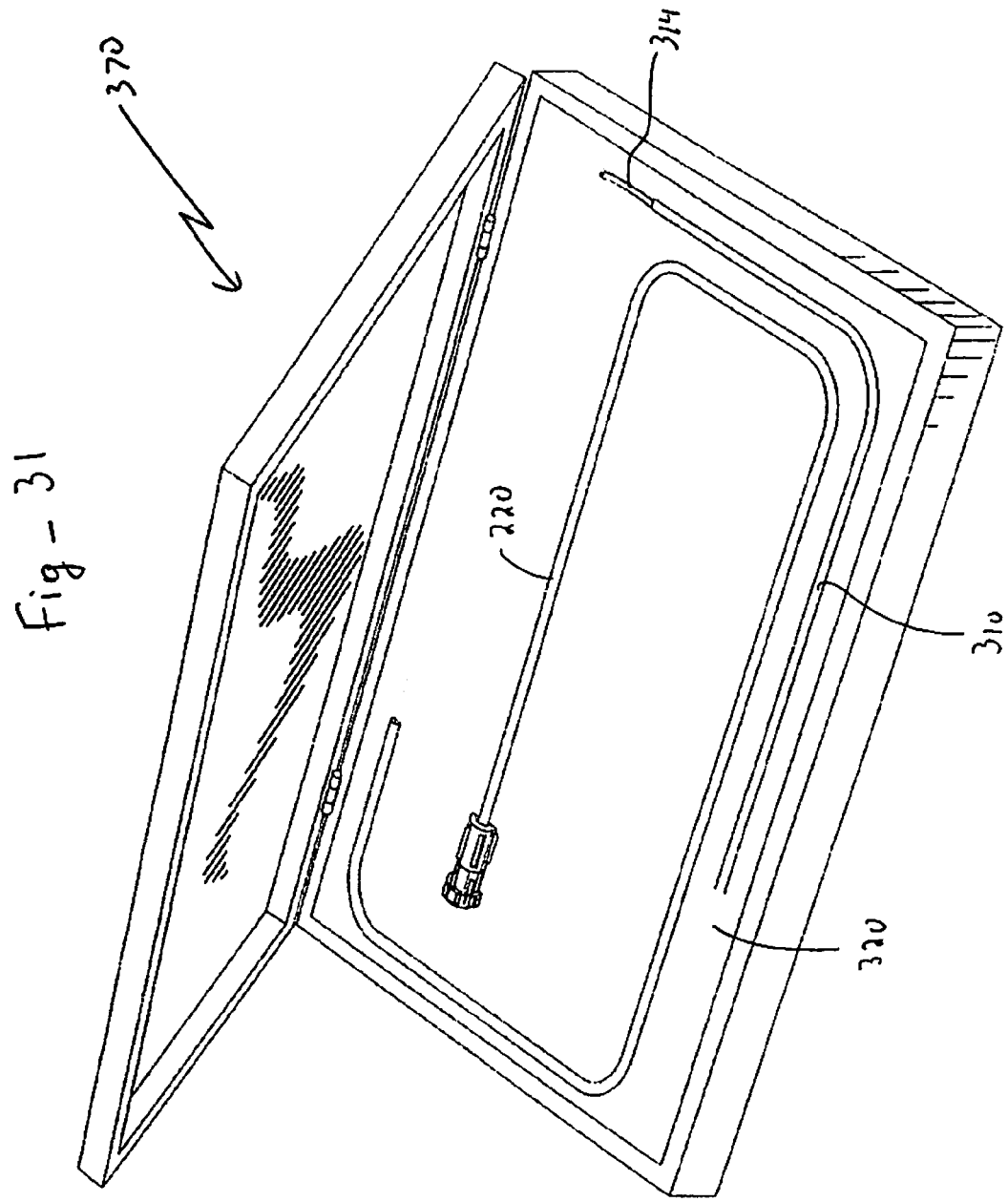

PERCUTANEOUS RENAL ACCESS SYSTEM

This application is a continuation in part of application Ser. No. 13/291,927, filed Nov. 8, 2011 now U.S. Pat. No. 8,771,287, which claims priority from provisional application No. 61/498,644, filed Jun. 20, 2011, provisional application No. 61/498,393, filed Jun. 17, 2011, provisional application No. 61/496,950 filed Jun. 14, 2011, provisional application No. 61/475,318, filed Apr. 14, 2011, provisional application No. 61/473,906, filed Apr. 11, 2011, provisional application No. 61/446,294, filed Feb. 24, 2011, provisional application No. 61/413,598, filed Nov. 15, 2010, provisional application No. 61/413,977, filed Nov. 15, 2010, provisional application No. 61/413,981, filed Nov. 15, 2010, provisional application No. 61/413,993, filed Nov. 16, 2010, provisional application No. 61/421,071, filed Dec. 8, 2010, provisional application No. 61/422,202, filed Dec. 12, 2010, and provisional application No. 61/424,041, filed Dec. 16, 2010. The entire contents of each of these applications was incorporated therein by reference.

We claim further priority from provisional application 61/570,987 filed Dec. 15, 2011, provisional application No. 61/563,969 filed Nov. 28, 2011, provisional application 61/588,509 filed Jan. 19, 2012, provisional application 61/597,828 filed Feb. 12, 2012, provisional application 61/600,936, filed Feb. 20, 2012. The entire contents of each of these applications are incorporated herein by reference.

BACKGROUND

1. Technical Field

This application relates to a percutaneous puncture system and more particularly to a percutaneous puncture system and method for creating a tract for nephrostomy tube creation.

2. Background of Related Art

Nephrostomy is the creation of a communication between the skin and kidney to provide for nephrostomy tube insertion. The objective in nephrostomy tube creation is to have the wire from outside the flank directed down the ureter to provide therapeutic drainage of an obstructed system. This allows for subsequent dilation of the tract, such as by a nephrostomy dilating balloon, between the kidney and the skin over a wire that extends down the ureter. The catheter and tract can also be used to facilitate stenting of a narrowed ureter or removal or treatment of stones obstructing the ureter. Current nephrostomy tube creation is dependent on x-ray exposure to guide the physician where to locate the nephrostomy puncture wire tract.

There are currently two widely used techniques for nephrostomy tube creation. One technique utilizes an antegrade approach. The antegrade approach holds increased bleeding risk due to the puncture needle puncturing the interlobar arteries as it passes into the collecting system. This antegrade approach is also skill intensive because it requires advancing from the flank to an "unknown" calyx. In fact, studies have shown that recent urology resident graduates often do not continue to perform the antegrade nephrostomy technique after graduating due to difficulty of this procedure. The procedure also requires a relatively large amount of radiation exposure.

The other technique commonly utilized is the Lawson technique. This technique is used to create a nephrostomy tract in a retrograde fashion. The Lawson technique is performed under fluoroscopy utilizing a deflecting wire inside a ureteric catheter to select the renal calyx to be entered. That is, fluoroscopy is used to identify the renal calyx for nephrostomy access. The Lawson technique is described for example in Smith's Textbook of Urology, 2007, BC Decker Inc., "Retrograde Access" by Dennis H. Hosking and is commercially available by Cook Urological, Inc. as the "Lawson Retrograde Nephrostomy Wire Puncture Set."

In the Lawson technique, a stainless steel 145 cm long guidewire (0.038 inches in diameter) having a 3 cm flexible tip is passed retrograde up the ureter into the renal pelvis under fluoroscopy. A 7 Fr catheter is passed over the guidewire into the renal pelvis and the guidewire is removed. A J-tipped wire in certain instances might be used to facilitate passage past an obstruction. Then the surgeon selects the optimal calyx for nephrostomy placement, optimization usually being defined by allowing easiest access to the renal calculi and the shortest tract.

Once the calyx is selected, the 0.045 inch diameter deflecting wire guide is inserted through the lumen of the catheter and twist locked to the proximal end of the catheter. Deflection of the wire tip deflects the tip of the catheter, and the catheter and attached wire can be advanced into the selected calyx. However, it is recognized that due to obstructions, e.g. presence of calculi, it may not be possible to advance the catheter into the optimally desired calyx and consequently a less optimal calyx is selected by the surgeon.

After insertion of the catheter into the selected calyx, the deflecting wire guide is removed from the lumen of the catheter, while maintaining the inner-calyx position of the catheter tip. A puncture wire and sheath as a unit are inserted through the catheter lumen, with the puncture wire sharp tip shielded by the sheath. During insertion through the catheter, the wire remains retracted within the sheath, and locked to the sheath by a pin vise lock, so its puncture tip is not exposed. The puncture wire and sheath are connected/locked to the proximal portion of the catheter. The puncture wire is then unlocked from the sheath, by untwisting the cap of the pin vise actuator to loosen the vise pin grip on the puncture wire, and then incrementally advanced from the distal end of the sheath through the flank, fascia and skin. After puncturing the skin, the puncture wire is advanced from below until approximately 15 cm of wire is externally visible.

The pin vise lock securing the puncture wire to the insulating sheath is then re-locked. A fascial incising needle may or may not be passed over the puncture wire at the flank to incise fascia, and is then removed. As the 7 French catheter is advanced through the cystoscope below, the puncture wire is drawn further out of the flank, until the tip of the 7 French catheter is delivered out of the flank. At this time, the 7 French catheter is unlocked from its connection to the puncture wire assembly, and the puncture wire and insulating sheath are removed from below. A 0.038" guidewire is then passed antegrade through the 7 French catheter from the flank, until it emerges out the lower end of the 7 French catheter at the cystoscope end. With this wire 'through and through' the body, the cystoscope and 7 French catheter are removed, leaving the guidewire in place.

The retrograde Lawson approach has several advantages over the antegrade approach including providing the surgeon an anatomic approach to the renal pelvis, increased likelihood of avoiding the interlobar arteries during puncture, and inherently having a wire down the ureter, an important step in securing control over the nephrostomy tract. It is also less skill intensive, due in large part to the fact that it enables travel from the "known kidney" to the "unknown flank/skin," which better respects the principles of surgery.

However, despite its advantages over the antegrade approach, there are several disadvantages to the Lawson technique. First, although requiring less radiation exposure, the patient is oftentimes still exposed to harmful doses of radiation. Secondly, it is often difficult to navigate the ureteric catheter beyond large obstructive stones in the renal pelvis. This inability to direct the catheter to the desired site (calyx) often leads the surgeon to access a less optimal calyx. Thirdly, fluoroscopy provides only a two dimensional view of the renal anatomy, thereby limiting the ability to confidently select the calyx for tract dilation. Sometimes, there is even uncertainty as to which calyx is actually chosen due to the limited visibility provided by fluoroscopy.

Consequently, it would be advantageous to provide a system and method that enables more precise calyx location, improves access to the calyx of choice, improves visualization, permits "fluoroscopy-free" calyx selection, and allows for preliminary laser lithotripsy of a portion of a stone that may block access to calyx of choice for nephrostomy creation. Also of significance is that nephrostomy tube creation procedures are usually performed by interventional radiologists, which can further compound the risks and problems since urologists usually have better success rates for selecting the calyx for such procedures. Thus, it would be advantageous if such improved system and method could be more commonly performed by urologists.

In an attempt to address some of the disadvantages of the Lawson technique, Dr. Larry C. Munch in an article entitled "Direct-Vision Modified Lawson Retrograde Nephrostomy Technique Using Flexible Ureteroscope" and published in the Journal of EndoUrology, Volume 3, Number 4, 1989, described a technique utilizing a flexible ureteroscope.

In this "Munch technique," a flexible steerable ureteroscope was utilized to inspect the renal pelvis and calices. As described, a flexible cystoscopy is performed and a 0.035 inch, 145 cm guidewire is passed into the ureteral orifice. Position within the ureter is assessed with fluoroscopy. The cystoscope is removed and a ureteral access sheath with its obturator is advanced over the guidewire, and the obturator is then removed and the ureteroscope is passed through the sheath into the renal pelvis. An appropriate calyx is chosen visually, and then the 0.0017 inch Lawson puncture wire and protective 3Fr radiopaque Teflon sheath is passed through the working channel of the ureteroscope. The calyx is entered and the sheath embedded in the wall of the calyx, and then the pin-vise lock which locks the puncture wire and sheath together is opened and the puncture wire is advanced through the skin under visual and fluoroscopic control. The puncture wire protective sheath and ureteroscope are then withdrawn, leaving the puncture wire and ureteral access sheath in place. At the skin, an 18 gauge needle is passed over the puncture wire into the kidney and then removed. A 9 French fascial dilator is then passed over the 0.017 inch puncture wire into the kidney, whereafter the puncture wire is removed and a 0.038 inch guidewire is passed through the 9 French dilator until it passes down the ureter through the access sheath, and exits through the urethra.

Although the Munch technique solves some of the problems associated with the Lawson technique, it is deficient in several respects. First, the Munch technique leaves the puncture wire exposed to the ureteropelvic junction. This creates the risk of cutting inside tissue, especially at the ureteropelvic junction, across which the very thin puncture wire passes. For example, tension on the puncture wire at the time of passing the antegrade exchange catheter may result in) internal 'slicing' of the ureteropelvic junction by the thin puncture wire. Second, at the time of deployment of the puncture wire, the Munch technique fails to secure the wire assembly and ureteroscope, forcing either the surgeon or an assistant to devote two hands to opening the pin-vise lock and advancing the puncture wire, all while holding the flexible ureteroscope in position in a selected calyx. This makes wire deployment cumbersome for the surgeon, less likely to be successful, requiring more skilled assistance, and increases the chances the tip of the flexible cystoscope will move out Of a selected location for nephrostomy creation. Third, Munch's technique of antegrade wire exchange is ineffectual and risks cutting the puncture wire with passage of 18 gage hollow bore needle over the wire. After passage of this needle, a 9 French fascial dilator is passed over the 0.017" puncture wire, representing a wire-catheter mismatch which can result in tearing of internal tissues. This large jump from an 18 gauge needle to a 9 French fascial dilator is also cumbersome and has a high chance of failing to grant access to the kidney.

Consequently, it would be advantageous to provide a system and method that would enable urologists to more economically and efficiently perform the nephrostomy procedure to obtain access for nephrostomy tube creation. Such procedure would have the above-noted advantages over the Lawson technique, e.g. improving calyx access, visualization etc., while also providing the advantages of reducing the number of surgical steps and securing the position of the components and protecting the puncture wire, especially at the ureteropelvic junction, thereby providing advantages over the Munch technique.

SUMMARY

The present invention overcomes the disadvantages and deficiencies of the prior art. The present invention provides in one aspect a method for creating a tract in retrograde fashion for nephrostomy tube creation comprising the steps of providing a puncture wire having a tissue penetrating tip shielded in a sheath, inserting the puncture wire and sheath through a channel in an ureteroscope, and securing the sheath to the ureteroscope. The method further includes the steps of advancing the puncture wire from the sheath while visualizing under direct vision the position of the puncture wire and advancing the puncture wire into a selected calyx with the sheath secured to the ureteroscope.

In preferred embodiments, the sheath and puncture wire are releasably locked together, and the method further comprises the step of releasing the puncture wire from the sheath, which in some embodiments can be achieved by unlocking a vise lock on the sheath.

Preferably, the method further comprises the step of selecting a calyx under direct visualization prior to advancing the puncture wire into the selected calyx.

The method can include the step of loading in antegrade fashion a sheath over the puncture wire with the ureteroscope remaining within a body of the patient.

In some embodiments, the method includes removing the sheath from the channel of the ureteroscope after the step of advancing the puncture wire through the calyx, flank and skin of a patient and subsequently inserting a second sheath through the channel over the puncture wire. The second sheath may have a tapered tip to facilitate passage through the renal capsule and flank fascia, and may be either a single or coaxial catheter. The second sheath can be advanced through the flank and in preferred embodiments is advanced after relocking the sheath to the puncture wire. In these embodiments, preferably subsequently the puncture wire is removed from the second sheath and a guidewire is advanced through the second sheath, or if of a coaxial design, after removal of the inner catheter, the guidewire is passed through the outer catheter of the coaxial catheter. In some embodiments, the first sheath and puncture wire are inserted in a first direction and the second sheath is inserted in the first direction after removal of the first sheath in a second direction.

The method may include the step of removing the puncture wire and ureteroscope from a body of the patient while leaving the sheath in position to subsequently receive a guidewire therethrough, the sheath functioning as an exchange sheath. In this embodiment, this first sheath may be a single catheter or a coaxial catheter. Where a coaxial catheter is used, the inner catheter is removed prior to passing the guidewire through the outer catheter.

In preferred embodiments, the method further comprises the step of providing a locking mechanism mountable to the ureteroscope wherein the locking mechanism has an opening to receive the sheath and puncture wire therethrough and is actuable to secure the sheath to the ureteroscope.

The method may also include the step of performing uteroscopic lithotripsy through the ureteroscope to remove a calyx blocking stone prior to inserting the puncture wire into the working channel of the ureteroscope.

In another aspect, the present invention provides a method for creating a tract for nephrostomy tube creation comprising the steps of:
 a) providing a puncture wire having a tissue penetrating tip shielded in a sheath, the puncture wire slidable within the sheath and releasably lockingly engaged thereto;
 b) inserting the puncture wire and sheath in a first direction through a working channel of an ureteroscope to exit the working channel of the ureteroscope;
 c) releasing the puncture wire from the sheath and advancing the puncture wire a first distance from the sheath while visualizing the position of the puncture wire;
 d) advancing the puncture wire and the sheath into a selected calyx and through the flank of a patient;
 e) removing the puncture wire from the sheath in a second direction different from the first direction; and
 f) inserting a guidewire through the sheath.

In some embodiments, the guidewire is inserted in a second direction through the sheath. In some embodiments, the sheath is of a coaxial design. In this embodiment, the inner catheter may be removed prior to advancing the guidewire through the outer catheter of the coaxial catheter set. The ureteroscope in some embodiments is removed in the second direction prior to the step of inserting a guidewire through the sheath.

In some embodiments, the puncture wire is first inserted through the flank and out the skin, and subsequently the sheath is advanced over the puncture wire through the flank. This can occur after re-locking the pin-vise mechanism. The sheath in this embodiment may be of a single catheter or a coaxial catheter. In other embodiments, the puncture wire is advanced a short distance from the sheath, e.g. approximately 1 cm, then re-locked to the sheath with the pin-vise, and the puncture wire/sheath duo are together inserted through the flank and out the skin and locked against sliding movement during insertion.

In some embodiments, after advancement of the puncture wire through the flank, the puncture wire is locked against movement. The puncture wire can have one or more markers thereon to indicate the extent of advancement from the sheath.

In another aspect, the present invention provides a method for creating a tract for nephrostomy tube creation comprising the following steps:
 a) providing a puncture wire having a tissue penetrating tip shielded in a first sheath, the puncture wire slidable within the first sheath and releasably lockingly engaged thereto;
 b) inserting the puncture wire and first sheath in a first direction through a working channel of an ureteroscope to exit the working channel of the ureteroscope;
 c) releasing the puncture wire from the first sheath and advancing the puncture wire a first distance from the first sheath while visualizing the position of the puncture wire;
 d) advancing the puncture wire and the first sheath from within a selected calyx and through the flank of a patient;
 e) removing the first sheath in a second direction different from the first direction;
 f) inserting a second longer sheath over the puncture wire through the channel of the ureteroscope with taper tip, possibly of coaxial design; and
 g) removing the puncture wire from the second sheath and ureteroscope.

In this method, preferably a guidewire is inserted through the second sheath after the step of removing the puncture wire from the second sheath.

The puncture wire can be relocked to the second sheath. In some embodiments, the second sheath is longer than the first sheath.

In some embodiments, the second sheath is inserted in the first direction; in other embodiments it is inserted in a second direction.

In yet another aspect of the present invention, a method of creating a tract for nephrostomy tube creation is provided which comprises the steps of providing a wire having a proximal end and a distal end with a puncture tip at the distal end, inserting the wire without a sheath directly into a working channel of an ureteroscope and advancing the wire from the channel so the puncture tip extends through the flank of a patient. Subsequent to advancement of the puncture tip through the flank, the method includes the steps of loading a sheath over the wire and through the working channel of the ureteroscope and thereafter removing the wire from the channel of the ureteroscope.

The method can further comprise the step of inserting a guidewire through the sheath after the step of removing the wire from the sheath and the channel of the ureteroscope. The sheath in some embodiments is loaded in an antegrade fashion; in other embodiments it is loaded in a retrograde fashion. The wire can be loaded initially through the proximal opening in the working channel. The method in some embodiments can include loading a dilation balloon over the guidewire.

The present invention also provides in another aspect a method for wire exchange to create a tract under direct visualization for nephrostomy tube creation while shielding the wire. The method comprises the following steps:
 a) providing a puncture wire having a tissue penetrating tip shielded in a first sheath;
 b) inserting the puncture wire and first sheath through a channel in an ureteroscope;
 c) advancing the puncture wire from the first sheath while visualizing under direct vision the position of the puncture wire;
 d) advancing the puncture wire into a selected calyx;
 e) removing the first sheath from the channel while leaving the ureteroscope in place to shield a portion of the wire that bends around the ureteropelvic junction to reduce tissue trauma;
 f) inserting a second sheath over the puncture wire while the puncture wire remains in the channel;
 g) advancing the second sheath from the channel under direct vision and out of the flank; and
 h) inserting a second wire through the second sheath after removal of the puncture wire therefrom.

In preferred embodiments, the first sheath is secured to the ureteroscope during the step of advancing the puncture wire into the selected calyx, and through the kidney and out the flank. Also, preferably, the puncture wire is releasably locked to the first sheath and subsequently releasably locked to the second sheath.

The present invention also provides in another aspect an exchange sheath for use with a working channel of an ureteroscope. The exchange sheath comprises a lumen dimensioned to slidingly receive a puncture wire having a penetrating tip and a first diameter, the puncture wire releasably locked to the exchange sheath. The puncture wire is movable distally out of the lumen of the exchange sheath to expose its penetrating tip to puncture tissue and movable proximally for separation from the sheath and removal from a patient's body with the sheath remaining in the body. The sheath is dimensioned to receive a guidewire through its lumen, while remaining in the body, the guidewire having a second diameter different, e.g. larger, than the first diameter of the puncture wire. The guidewire is receivable through the lumen of the sheath. In some embodiments, the sheath is of a coaxial design. In this embodiment, the inner catheter may be removed prior to advancing the guidewire through the outer catheter of the coaxial catheter set.

In preferred embodiments, the sheath remains in the working channel of the ureteroscope during insertion of the guidewire therethrough. In some embodiments, the sheath has a diameter of between about 0.038 to about 0.052 inches. In some embodiments, the sheath has a length of about 90 cm to about 115 cm. The puncture wire can have a length of about 90 cm to about 165 cm.

In some embodiments, a first locking mechanism for locking the puncture wire and sheath can be provided and a second locking mechanism for locking the sheath and the ureteroscope can be provided.

In some embodiments, the sheath locking mechanism comprises a clamping member having an opening of a first dimension, the opening changeable to a second dimension to provide a clamping force on the sheath. The locking mechanism can be mounted directly to the ureteroscope. The locking mechanism can be releasably mounted to the sheath.

In another aspect, the present invention provides a system for accessing a select calyx for kidney surgery comprising a flexible ureteroscope having a proximal portion and a distal portion, and a wire having a penetrating tip at a distal end. The wire is configured and dimensioned for insertion through the ureteroscope and advanceable distally of the distal portion of the ureteroscope for visualization of the wire. The wire is insertable and advanceable through the ureteroscope without a protective sheath.

The system may further comprise a sheath advanceable into the ureteroscope subsequent to advancement of the wire through a flank of a patient. In some embodiments, the puncture wire has a diameter of about 0.013 inches to about 0.025 inches.

Also provided, in another aspect, is a system for accessing a select calyx for kidney surgery comprising a first wire having a penetrating tip at a distal end and having a first diameter and configured and dimensioned for insertion through a channel of an ureteroscope. The wire is advanceable distal of a distal opening in the channel of the ureteroscope for visualization of the wire. An exchange sheath shields at least a portion of the first wire, and the first wire is slidable with respect to the exchange sheath so the penetrating tip is movable from a retracted shielded position to an exposed unshielded position, the first wire being fully separable and removable from the sheath. The exchange sheath is configured and dimensioned to receive a second wire having a second diameter different, e.g. larger, than the diameter of the first wire to enable wire exchange without removal of the exchange sheath.

In preferred embodiments, the wire is lockingly engageable with the exchange sheath and the sheath is lockingly engageable with the ureteroscope. In some embodiments, the exchange sheath is lockingly engageable with the ureteroscope. The wire can include one or more markers to indicate the extent of distal movement relative to the sheath.

In some embodiments, the second wire is a guidewire having a diameter of between about 0.020 inches and about 0.038 inches, the first wire has a length of about 90 cm to about 165 centimeters and the sheath has a length of about 80 cm to about 110 centimeters.

In another aspect of the present invention, a system is provided for accessing a select calyx for kidney surgery comprising a wire having a penetrating tip and a first diameter and configured and dimensioned for insertion through an ureteroscope. The wire is advanceable distal of the distal portion of the ureteroscope for visualization of the wire. A sheath shields at least a portion of the wire. The wire is slidable with respect to the sheath so the penetrating tip is movable from a retracted shielded position to an exposed unshielded position, the wire fully separable and removable from the sheath. The system includes a mechanism for mounting the sheath to the ureteroscope.

In some embodiments, the sheath is removable from the working channel of the scope with the wire remaining within the working channel.

In some embodiments, the wire is removable from the sheath leaving the sheath within the working channel of the ureteroscope.

In some embodiments, the sheath mounting mechanism includes a locking member with a clamping member to apply a clamping force on the sheath. In some embodiments, rotational movement of a control constricts an opening in the clamping member. The wire can include one or more markers to indicate the extent of distal movement relative to the sheath. The system can include a locking mechanism for releasably locking the wire to the sheath.

In some embodiments, the sheath is about a 3 Fr sheath and can have a length exceeding about 90 centimeters. The sheath can have a radiopaque tip.

The system can further comprise a coaxial dilator and a sheath.

In yet another aspect, the present invention provides a device for retrograde access to and advancement through the calyx and antegrade access to the bladder, the device comprising a wire having a tissue penetrating tip and a sheath encasing the tip, the wire having a length in the range of about 135 cm to about 160 cm to enable insertion through a working channel of a ureteroscope and advancement through a flank of a patient, and a sheath having a length in the range of about 80 cm to about 120 cm to enable locking engagement with the ureteroscope while enabling exit through the distal end of a ureteroscope and through the flank of the patient.

The device may further include a marker(s) on the wire to indicate the extent of advancement of the wire. The device may include a first locking mechanism for locking the puncture wire and sheath and a second locking mechanism for locking the sheath and the ureteroscope.

The present invention in another aspect provides a kit comprising a) a puncture wire having a first diameter and a first sheath having a first length, the puncture wire slidable with respect to the first sheath, and the sheath removable from the puncture wire; and b) a second sheath having a second length greater than the first length of the first sheath, the second sheath slidable over the puncture wire and dimensioned to receive a second wire having a second diameter greater than the first diameter.

In some embodiments the second wire has a diameter of about 0.035 inches to about 0.038 inches and the first wire has a diameter of about 0.017 inches. In some embodiments, the first sheath has a length of about 85 cm to about 120 cm, the second sheath has a length of about 100 cm to about 115 cm and/or the puncture wire has a length of about 90 cm to about 165 cm.

In another aspect, the present invention provides a method for creating a tract in retrograde fashion for nephrostomy tube creation comprising the steps:
  a) providing a puncture wire having a tissue penetrating tip shielded in a sheath;
  b) inserting the puncture wire and sheath through a channel in an ureteroscope;
  c) advancing the puncture wire from the sheath while visualizing under direct vision a position of the puncture wire;
  d) advancing the puncture wire through a selected calyx; and
  e) inserting antegrade a coaxial catheter over the puncture wire.

In some embodiments, the sheath and puncture wire are releasably locked together, and the method further comprises the step of releasing the puncture wire from the sheath. Preferably, the method includes the step of selecting a calyx under direct visualization prior to advancing the puncture wire into the selected calyx.

The method may further include the steps of a) advancing the puncture wire through a flank and skin of a patient; and b) removing the sheath from the channel of the ureteroscope after the step of advancing the puncture wire through the flank and skin of the patient.

In some embodiments the method further includes the step of inserting a wire antegrade though a lumen of the outer catheter of a coaxial catheter set; in other embodiments, the method further includes the step of inserting two wires antegrade though a lumen of the outer catheter of a coaxial catheter set.

In some embodiments, the coaxial catheter includes an inner catheter locked to an outer catheter.

The method can further include the step of observing markings on the puncture wire to determine an exposed length of the puncture wire.

The method can further include the step of providing a locking mechanism mountable to the ureteroscope, the locking mechanism having an opening to receive the sheath and puncture wire therethrough and actuable to secure the sheath to the ureteroscope.

The method can further include the steps of removing the puncture wire and an inner catheter of the coaxial catheter, leaving the outer catheter in place extending through a ureter of a patient.

In accordance with another aspect of the present invention a method is provided for exchanging a puncture wire for a working wire in creating a tract for nephrostomy tube creation comprising the steps:
  a) providing a puncture wire having a tissue penetrating tip shielded in a sheath, the puncture wire slidable within the sheath and releasably lockingly engaged thereto;
  b) inserting the puncture wire and sheath in a first direction through a working channel of an ureteroscope to exit a channel of the ureteroscope;
  c) releasing the puncture wire from the sheath and advancing the puncture wire a first distance from the sheath;
  d) advancing the puncture wire and the sheath into a selected calyx and through a flank of a patient;
  e) removing the sheath in a second direction different from the first direction;
  f) inserting over the puncture wire in the second, direction a coaxial catheter having an outer catheter and an inner catheter positioned therein;
  g) removing the puncture wire from the coaxial catheter; and
  h) inserting a wire in the second direction through the coaxial catheter.

The method can further include the step of inserting another wire in the second direction through the coaxial catheter.

The method can further include the step of removing the puncture wire and the inner catheter prior to the step of inserting the wire.

In some embodiments, the puncture wire has at least one marker thereon to indicate an extent of advancement relative to a patient's skin.

The present invention also provides in another aspect a system for accessing and advancing through a select calyx for nephrostomy tube creation. The system comprises a first wire having a penetrating tip at a distal end, the first wire having a first diameter and configured and dimensioned for insertion through a channel of an ureteroscope and advanceable distal of a distal opening in the channel of the ureteroscope for visualization of the first wire. A sheath shields at least a portion of the first wire, the first wire slidable with respect to the sheath so the penetrating tip is movable from a retracted shielded position to an exposed unshielded position, and the first wire is fully separable and removable from the sheath. A coaxial catheter is provided having an outer catheter and an inner catheter removably positioned therein. The inner catheter has a first internal lumen configured and dimensioned for advancement over the penetrating tip of the first wire to minimize the outer diameter at its tip to permit passage through the renal capsule and body fascia, i.e. aiming for zero clearance in relation between the first wire and inner catheter of the coaxial set. The inner catheter is advanceable over the first wire and the outer catheter that preferably has a zero clearance between its tip and the outer surface of the inner catheter. The outer catheter has a second internal lumen configured and dimensioned to receive at least one working wire therethrough after removal of the inner catheter and an outer diameter configured to minimize difficulty passing catheter through flank fascia and renal capsule.

In some embodiments, the at least one working wire is a guidewire having a diameter of between about 0.025 inches and about 0.038 inches, the first wire has a length of about 90 cm to about 165, and the sheath has a length of about 80 centimeters to about 110 centimeters.

In some embodiments, the at least one working wire includes two wires insertable through the second internal lumen.

The system may include a first locking mechanism for locking the puncture wire and sheath and a second locking mechanism for locking the sheath and the ureteroscope.

The first wire can include a marker to indicate an extent of distal movement.

In accordance with another aspect, the present invention provides a kidney access kit comprising a coaxial catheter and a puncture wire having a first outer diameter and a first sheath having a first length, the puncture wire slidable with respect to the sheath, and the sheath removable from the puncture wire.

The coaxial catheter includes an outer catheter and an inner catheter slidably positioned therein, and having an outer diameter closely matching an inner diameter of the outer catheter, the inner catheter having an internal lumen having a diameter closely matching but slightly greater than the first outer diameter of the puncture wire and dimensioned to slide over the puncture wire and the outer catheter dimensioned to receive a second wire having a second diameter greater than the first diameter.

In some embodiments, the second wire has a diameter of between about 0.035 to about 0.038 inches. In some embodiments, the outer catheter of the coaxial catheter has an outer diameter of about between about 0.038 inches to about 0.052 inches.

In alternate embodiments, the wire serves dual function—puncture and working wire. Wire construction may be modified to decrease the risk of injury to ureteropelvic junction and other structures when such structures are exposed to the puncture wire. With this, a fully deployed puncture wire that has passed through the flank could be kept in place, even after removal of insulating protective sheath, leaving the wire exposed to the ureteropelvic junction for continuation of the next procedural step e.g. balloon nephrostomy passage over this wire for tract dilation or advancement of a larger coaxial catheter for passage of a second wire, or even exchange of the puncture wire for one or two other wires.

The altered construction puncture wire is contemplated to have the following properties (among other):
  1. wire is adequately deflectable so that flexible tip of ureteroscope can be actively deflected with wire positioned at the end of ureteroscope working channel
  2. wire will pass easily through fascia and flank
  3. minimize risk of injury to adjacent organs from errant puncture wire passage e.g. through liver, spleen, colon.
  4. have low risk of slicing through collecting system e.g. ureteropelvic junction when uncovered puncture wire is pulled taut across these structures
  5. The wire and its sheath must be of small enough diameter to pass through a ureteroscope operating channel.

Methods to accomplish this are several and include the following:

First, the puncture wire diameter could be increased in a uniform fashion from a minimum of 0.023" up to a maximum of 0.035". This can be accomplished by using a single property wire that has a sharp tip to pass through tissues, sufficient column strength, and enough diameter to minimize risk of incising through body tissues e.g. ureteropelvic junction. Diameter of such a wire is anticipated to be between 0.020 to 0.038" in uniform diameter. Material construction may include stainless steel, nickel titanium (nitinol), composite wire material, or Other materials.

Second, a variable property puncture wire is described herein. The wire contemplated has a distal and a proximal segment. The entire wire length may be 85-120 cm, preferably 95-110 cm.

The distal segment (FIG. 3-1) may be composed of stainless steel (or other metals e.g. composites, tungsten, nickel, etc). The wire has a sharpened tip (FIG. 3-2). Diameter of this segment ranges between 0.013" to 0.038", preferably 0.017"-0.020". Other metals are considered as well. Properties needed for the distal segment include:
  1. Sharp tip
  2. Sufficient column strength to permit advancement through kidney, flank
  3. Thin and relatively smooth, in order to ease passage through tissues and minimize damage to adjacent organs if inadvertently punctured.
  4. Potential for coating or brushing/scratching/dimpling to increase ultrasound visibility. Other techniques, including tungsten, platinum, ceramic or other construction, could be considered, to increase ultrasound visibility.
  5. Length of distal segment will be between 5 and 30 cm length, preferably between 12 and 30 cm.

The proximal segment measures between 70-110 cm. It is likely thicker than the distal segment, and must be resistant to kinking. This segment as a diameter ranging between 0.020" and 0.045", preferably between 0.025" and 0.038".

This segment will be exposed to the ureteropelvic junction, ureter, bladder, and uretha. When pulled taut, even overly so, it must have property to NOT cut through these tissues as would the 0.017" stainless steel puncture wire. It must also be resistant to kinking. This wire will either have (1) nephrostomy tract dilator—balloon or manual serial dilators, or (2) coaxial catheter for wire addition and/or exchange passed over it.

Achieving a thinner distal segment compared to proximal segment can be accomplished in several ways. Possibilities include but are not limited to:
  1. Wire coiling around thin puncture wire (e.g. 0.017" stainless steel wire), where such coil is not applied to the distal segment of this wire. This coil can be laser welded to the inner core steel wire at 5-15 cm intervals to help reduce 'kinking' of proximal, wider segment. This wire coiling would add diameter and kink resistance to the proximal segment. This can be alternatively accomplished using a helical hollow strand. There can be 1, 2, or 3 layers, and/or with filar count ranging from 6-18. Materials may include 302, 35N LT, CP titanium, Pt Alloys, 304V, DFT, Ti6Al-4V EL1, 316L, L-605, Nitinol. Other metals or materials are considered. As such, the thin puncture wire runs through the entire variable wire, and the proximal 60-80% of this wire is coil-wrapped to thicken it.
  2. Proximal segment wire may be coated with material that would increase the wire caliber e.g. nitinol or other material. This coating would not be applied to the distal segment wire that is used to puncture kidney, flank, and skin.
  3. Entire wire may be of a uniform construction, however the distal segment may be tapered down to smaller diameter compared to proximal aspect of wire, possibly by 'grinding' down the distal segment, or by other methods to achieve a thinner distal segment than the longer, proximal section of wire. Tip would be sharpened.

The transition segment from narrow distal wire segment to thicker proximal wire segment (FIG. 3-3) can range from 0.5-5 cm in length. Ideally, it has a smooth transition rather than a 'shelf', to permit smooth passage through body tissues.

Third, a coaxial wire is considered with a moveable core, where the inner core is the puncture wire that is sharp and thin, and the outer coaxial component is a coil construction wire that can be releasably locked and moved in relation to the outer puncture wire. After puncture with the exposed, thin, distal inner wire, the two elements, inner and outer coaxial wires, are locked in relation to each other, and the wire is further advanced out of the flank. Wire softness (opposite of rigidity) and kink resistance can be increased potentially by removing the inner core after puncture of skin.

In alternate embodiments, or combined with embodiments described herein, all or part of puncture wire may be designed to have enhanced ultrasound visibility. These may allow for reduced radiation exposure during nephrostomy creation by allowing ultrasound guided confirmation of wire location during deployment. Options to achieve this include, but are not limited to constructing at least the puncture (distal) wire segment of, or with component of a highly ultrasound-visible metal or other material. Examples include, but are not limited to, platinum or tungsten. These components may be mixed with stainless steel as an alloy or simply the distal tip of the wire can be made of these materials. Alternatively, this segment or entire wire can be coated ceramic material, tungsten, platinum, other metals or polymers, or other material that has been treated or impregnated with microbubbles.

In an alternate embodiment, after successful wire puncture out of the flank, a coaxial catheter can be passed retrograde, in the same direction as the puncture wire passage, to be delivered out of the flank from within the patient. This catheter is passed over the puncture wire. This can be performed through the operating channel of the ureteroscope over the puncture wire or over the unprotected puncture wire after removal of the ureteroscope. Alternatively, the coaxial catheter serves a dual function of protective sheath and wire exchange system. A device is contemplated whereby a releasable lock, preferably a pin-vise lock, is related to the inner catheter of the coaxial set with a fixed or removable locking mechanism. The outer catheter is related to the inner catheter of the coaxial set with a releasable locking mechanism, preferably a Luer lock. In this case, the pin-vise lock or other locking mechanism relates the puncture wire to the inner coaxial catheter. The coaxial catheter functions as the protective sheath that shields the ureteroscope operating channel from damage from the puncture wire tip during passage through the operating channel. This is accomplished by locking the puncture wire position just inside the tip of the inner catheter. After the puncture wire/coaxial sheath ensemble is advanced through the operating channel of the ureteroscope and out of the distal end of the ureteroscope, the releasable lock mechanism relating the puncture wire to the inner catheter is released and the puncture wire is advanced out of the tip of the inner coaxial catheter, where it was positioned prior to deployment. If the puncture wire site is accepted, the releasable locking mechanism relating the puncture wire to the coaxial set is locked and the entire ensemble is advanced further in the same direction until out of the flank. The inner and outer coaxial catheters are then released from each other by opening the Luer lock or other releasable locking mechanism. The inner catheter and puncture wire are removed in the direction opposite their initial passage, leaving the outer coaxial catheter in position from outside the urethra to outside the flank. A standard working wire (0.025" to 0.038") is then passed either antegrade or retrograde through the outer coaxial catheter until the wire is 'through and through' from outside the flank to out of the urethra. The outer coaxial catheter is then removed.

BRIEF DESCRIPTION OF THE DRAWINGS

Preferred embodiment(s) of the present disclosure are described herein with reference to the drawings wherein:

FIG. 1 is a perspective view of a first embodiment of the puncture wire and sheath of the present invention;

FIG. 1A is a perspective view of an alternate embodiment of the puncture wire and sheath of the present invention;

FIG. 2 is a side view illustrating the pin vise lock for locking the sheath and puncture wire together;

FIG. 3 illustrates initial insertion of the puncture wire and sheath of FIG. 1 through a working channel of a flexible ureteroscope positioned through the ureter and extending into the kidney, for clarity the ureteral access sheath not shown;

FIG. 4 illustrates the ureteroscope inserted through a selected calyx and the sheath and puncture wire being advanced through the ureteroscope;

FIG. 5 is a view similar to FIG. 4 showing a portion of the ureteroscope of FIG. 1 and showing further insertion of the puncture wire and sheath through the ureteroscope with the sheath and puncture wire extending distal of the ureteroscope;

FIG. 5A is a view similar to FIG. 5 illustrating the puncture wire advanced through the flank and skin;

FIG. 6 is a view similar to FIG. 3 corresponding to the position of the puncture wire and sheath of FIG. 5A with the sheath locked to the ureteroscope;

FIG. 7 is a view similar to FIG. 5A illustrating the puncture wire further extended through the skin and the sheath advanced over the puncture wire through the flank and skin;

FIG. 8 is a close up view of the sheath locking mechanism;

FIG. 9 is a cross-sectional view taken along line 9-9 of FIG. 8;

FIG. 10 is a view similar to FIG. 7 illustrating withdrawal of the puncture wire from the sheath;

FIG. 12 is a perspective view of one embodiment of a kit of the present invention;

FIG. 13 is a perspective view of an alternate embodiment of the puncture wire and sheath of the present invention;

FIG. 14 is a cross-sectional view taken along line 17-17 of FIG. 14 showing the pin vise lock clamping the puncture wire;

FIG. 15 illustrates initial insertion of the puncture wire and sheath of FIG. 13 through a flexible ureteroscope positioned through the ureter and extending into the kidney;

FIG. 16 illustrates the ureteroscope inserted through a selected calyx and the sheath and puncture wire of FIG. 13 being inserted through the ureteroscope;

FIG. 17 is a cross-sectional view taken along line 17-17 of FIG. 13 illustrating release of the pin vise lock to allow movement of the puncture wire within the sheath;

FIG. 18 is a view similar to FIG. 15 illustrating the puncture wire advanced through the flank and skin;

FIG. 19 is a view similar to FIG. 16 illustrating further advancement of the puncture wire from the sheath;

FIG. 20 is a view similar to FIG. 19 illustrating the puncture wire within the ureteroscope after withdrawal of the sheath from the ureteroscope and patient's body;

FIG. 21 is a view similar to FIG. 20 illustrating insertion of a second wire through the sheath after a second longer sheath has been advanced over the puncture wire through the flank and skin and the puncture wire and ureteroscope have been removed from the body;

FIG. 22 is a perspective view of another embodiment of a kit of the present invention;

FIG. 23 is a side view of an alternate embodiment of the puncture wire shown extending through the skin;

FIG. 25A is a side view of a first embodiment of a coaxial catheter;

FIG. 25B is a side view of a second embodiment of a coaxial catheter;

FIG. 26 illustrates the puncture wire, and sheath extending through a working channel of a flexible ureteroscope that is positioned through the ureter and extending into the kidney, the puncture wire shown extended through the flank and skin (for clarity the ureteral access sheath is not shown);

FIG. 26A is a broken side view of an alternate embodiment of the puncture wire of FIG. 26 illustrating length markings on the wire;

FIG. 27 is a view similar to FIG. 26 illustrating cutting the bent distal tip of the puncture wire;

FIG. 28 is a view similar to FIG. 27 illustrating antegrade loading of the coaxial catheter of FIG. 25A over the puncture wire, the coaxial catheter being passed into the kidney and down the ureter;

FIG. 30 is a view similar to FIG. 29 showing an alternate embodiment where two separate wires have been passed through the outer catheter of the coaxial catheter, and the outer catheter has been subsequently removed; and FIG. 31 is a perspective view of an alternate embodiment of a kit of the present invention.

DETAILED DESCRIPTION OF PREFERRED EMBODIMENTS

Figure 11:
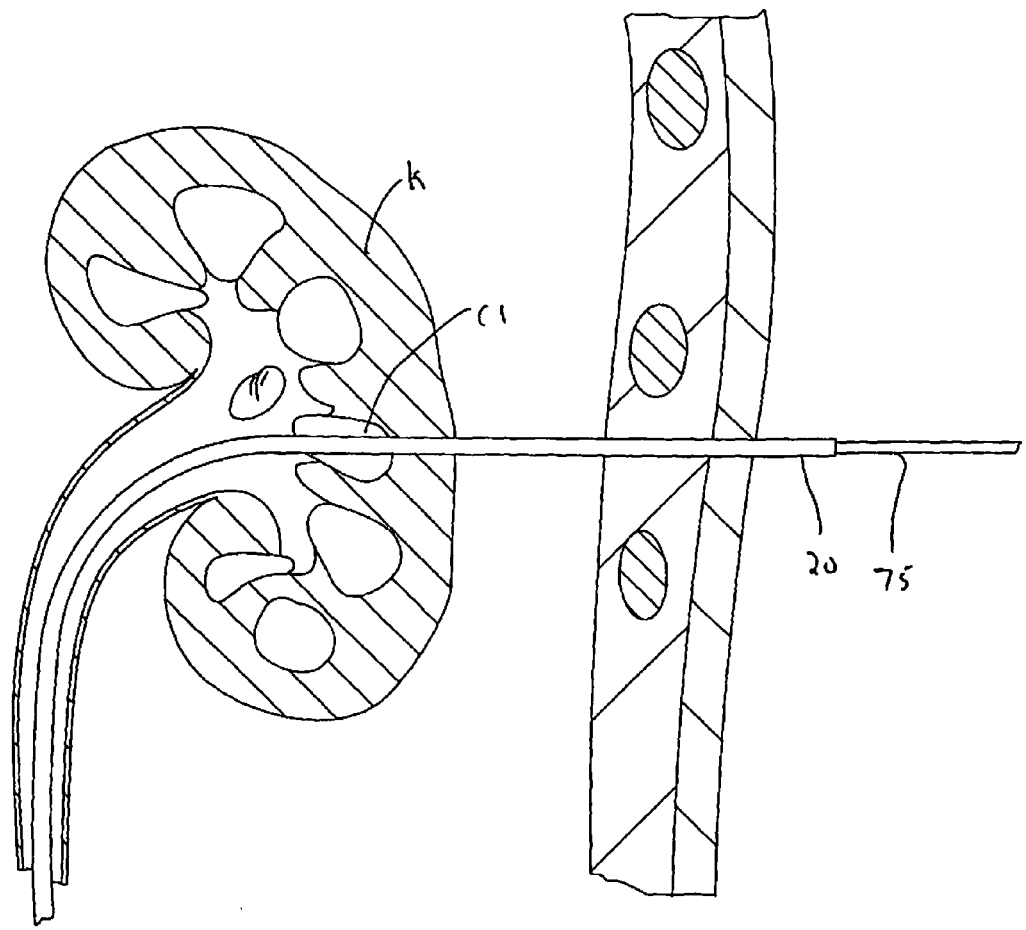
FIG. 11 is a view similar to FIG. 10 illustrating insertion of a guidewire through the sheath.

Referring now in detail to the drawings wherein like reference numerals identify similar or like components throughout the several views, FIGS. 1-31 illustrate various embodiments of the present invention. The present invention provides accessing as well as selecting a calyx under direct visualization utilizing an ureteroscope in order to create a nephrostomy tract for nephrostomy tube creation.

A puncture wire is advanced through a working channel of an ureteroscope which has been passed into the kidney in retrograde fashion. The puncture wire is then deployed from the ureteroscope working channel through a surgeon selected calyx and through the kidney and out the flank and skin in a retrograde fashion. This technique obviates the need for antegrade access to the calyx as antegrade access disadvantageously requires significant technical skill due to advancement into the "unknown calyx" and creates potential risks for the patient including relatively high radiation exposure. This retrograde visualization approach of the present invention, as will become apparent from the detailed description below, not only provides improved visualization, but provides such improved visualization while securing/locking the positions of the sheath and wire with respect to the ureteroscope and ensuring the wire is protected from damaging tissue during the procedure. Further, the present invention, as also discussed below, enables a streamlined approach to breaking an obstructing stone with laser and gaining access to the desired calyx which might otherwise be blocked and access denied.

Two systems and methods are provided by the present invention, both utilizing a puncture wire and a protective sheath such as 3Fr radiopaque PTFE sheath. In the first system described herein, the sheath which protects the puncture wire during insertion is also used as an exchange sheath so that the puncture wire can be withdrawn and a guidewire inserted into the sheath. This sheath can be of single catheter or of coaxial catheter design. This simplifies the components and procedural steps of the surgery. In the second system described herein, two sheaths are utilized: a first protective sheath to protect the puncture wire during insertion and a second sheath to replace the first protective sheath so that the puncture wire can be withdrawn and a guidewire inserted through the second sheath. Both these systems and methods of using the system are described in detail below.

The present invention also provides another system and method utilizing a coaxial catheter. The coaxial catheter is passed over the puncture wire and then one or more replacement wires are inserted antegrade through the coaxial catheter. This system and method is also described in detail below.

Turning initially to the first system and method which is illustrated in FIGS. 1-13, the system includes a protective sheath 20 and a puncture wire 30. Sheath 20 has a lumen 22 extending therethrough dimensioned to slidingly receive the puncture wire 30 therein. That is, puncture wire 30 is received within the sheath lumen 22 for sliding movement from a retracted position wherein the puncture (penetrating) tip 32 of wire 30 is protected (shielded) by the sheath 20 (see e.g. FIG. 4) and an extended position where the puncture tip 32 is exposed from the sheath 20 to penetrate tissue (see e.g. FIG. 5) as the puncture tip 32 extends beyond the distal opening of the sheath 20. Exposure of the puncture wire tip 32 enables advancement of the wire 30 through the flank and skin as described below.

The puncture wire 30 and sheath 20 are releasably locked together by a conventional vise lock 50. As shown, with reference to FIGS. 1 and 2, vise lock 50 has a rotatable actuator 52 and a metal locking tube 54 with a longitudinally extending elongated slot 55. A first (distal) portion 54a of locking tube 54 is seated within tube 56; a second opposite proximal portion 54b is seated within the actuator 52 (FIG. 2). Actuator 52 has reduced diameter portion 52a threadingly received in tube 56 and a lumen 57 through which the wire 30 extends. When actuator 52 is rotated within tube 56, it clamps down on the metal locking tube 54 reducing its diameter due to the slot 55, to thereby clamp down on the wire 30 to lock it from sliding movement with respect to the sheath 20. Consequently, as described below with respect to the method of use, the wire 30 and sheath 20 can be locked together so they can be advanced as a unit through the ureteroscope. When it is desired to move the puncture wire 30 relative to the sheath 20, the actuator 52 is unscrewed from tube 56, thereby releasing the clamping force on the metal tube 54 so the wire 30 can slide relative to the sheath 20. A reinforcement tube 58 extends distally from distal tube 59 which can connect via screw threads (or by other methods).

The region of the sheath 20 adjacent the vise lock can include a strengthened region to help stabilize the system. The strengthening can be achieved by thickening, reinforcing or hardening the sheath in this region (see e.g. reinforcement tube 27 of FIG. 3). This would reduce the movement of the pin vise during puncture wire deployment. That is, once this strengthened region is passed into the channel, the Tuohy-Borst type port adaptor and port is tightened, the pin-vise lock above (proximal) this level will be more stabilized.

The system also includes a sheath locking mechanism 60 (see e.g. FIGS. 3, 8 and 9) for locking the sheath 20 to a working channel of the ureteroscope 40. This is described in more detail below.

A conventional ureteroscope is designated generally by reference numeral 40 in FIGS. 3-6 and includes a working (operating) channel opening 46 communicating with channel (lumen) 42. The ureteroscope 40 is preferably a steerable scope so it can be articulated through the urinary system to gain access to the desired calyx. More specifically, the working channel 42 is accessible through an opening in side arm or port 44 which communicates with the ureteroscope channel 42 extending longitudinally within the length of the ureteroscope 40. The ureteroscope 40 provides both illumination and visualization of the surgical site as well as illumination and visualization of the puncture wire 30 and sheath 20 as they are advanced from the distal opening 47 of the ureteroscope 40, thus providing visualization of the system components as well as the patient's body. The ureteroscope 40 typically has a working channel length of about 60 cm to about 66 cm plus a portion of working channel length within the handle of ureteroscope of about 12 cm to about 16 cm (total working channel length about 75 cm to about 82 cm), a total outer diameter at the tip of about 5 French to about 8.1 French, with a working channel diameter of about 3 French to about 4.5 French. The working channel 42 is also dimensioned to receive a laser fiber for reducing blocking stones as described below. The ureteroscope is preferably inserted through a ureteral access sheath (not shown).

Note the port 64 of the scope 40 prevents irrigation fluid leakage from the working (operating) channel, and preferably can include a Tuohy-Borst type adapter which seals around instrumentation (e.g. the sheath) inserted therethrough. It can also tighten around the protective sheath with a circumferentially tightening O-ring mechanism.

Sheath locking mechanism 60, as shown in FIG. 3, is mounted to side port 44 of ureteroscope 40. With reference to FIGS. 8 and 9, sheath locking mechanism 60 includes a scope mounting portion 62 having a tubular extension at its distal portion for insertion into the working channel 42 of the ureteroscope 40. The distal portion can have a threaded end for threading into the opening 46 of the working channel 42 or alternatively can be snap fit into opening 46 to attach the mounting portion 62 to the ureteroscope 40. A lumen extends though the mounting portion 62 and contains a flexible O-ring 68 positioned therein. The sheath 20 extends though the lumen and through the opening in the O-ring 68. When threaded locking knob 64 is rotated, it provides a clamping force on the threaded cylinder 66 which clamps down on the O-ring 68 to reduce the size of its opening, thereby clamping down on the sheath 20 to lock it into position, i.e. lock it against movement with respect to the ureteroscope 40. Note the clamping force is sufficient to secure the sheath 20, but limited to not lock the wire 30 positioned therein, thereby still enabling sliding movement of the wire 30 with respect to the sheath 20. This locking of the sheath 20 to the ureteroscope 40 advantageously enables the sheath position to be maintained while the surgeon manipulates the puncture wire 30, as described in more detail below in conjunction with the method.

It should be appreciated that the sheath locking mechanism 60 can be provided on the sheath 20 as packaged, or alternatively provided as a separate component. If provided as a separate component, it can optionally be packaged with the sheath 20 in a kit.

It should be appreciated that other mechanisms for locking the sheath 20 to the ureteroscope 40 are also contemplated which would retain the sheath position during surgery. For example, the puncture wire/sheath duo could mate and lock directly onto the ureteroscope working channel port either by prior removal of the nipple and directly locking the Luer lock end of the pin-vise apparatus to the working channel, or by locking the pin-vise apparatus onto a separate device that interfaces with the working channel port and puncture wire/sheath duo.

Note the portion of the protective sheath 20 nearest the pin vise lock 50 may be made stiffer so that when locked in position by clamp 64, there would be less motion of the pin vise mechanism during deployment of the puncture wire 30 by the surgeon. One way to achieve this is shown in FIG. 1A where tube 69 is positioned over the sheath 20.

The sheath 20 preferably has a length of between about 70 cm to about 120 cm, and more preferably about 100 to about 115 cm. With this length, the sheath 20 has sufficient length for insertion through the entire working channel 42 of the ureteroscope 40, which typically has a length of approximately 75 cm including the portion of channel within the ureteroscope handle, as well as sufficient length to exit therefrom and extend through the flank and skin. The sheath is preferably a 3 French sheath, having an internal diameter that is sufficient to receive both the puncture wire 30, and a subsequent 0.025 to 0.038 inch guidewire through the lumen 22. Other dimensions are also contemplated such as sheath diameters of between about 0.038 inches and about 0.052 inches. The sheath is preferably composed of PTFE (e.g. polyimide or similar), although other materials are also contemplated.

The puncture wire 30 preferably has a length of between about 110 cm to about 165 cm, and more preferably a length of about 145 cm. The wire 30 preferably has a diameter ranging from about 0.013 inches to about 0.025 inches, and preferably a diameter of about 0.017 inches, sized to enable sliding movement within sheath lumen 22. With this length, the puncture wire 30 has sufficient length for insertion through the entire working channel 42 of the ureteroscope 40 as well as sufficient length to exit therefrom and extend through the flank and skin. The puncture wire can be composed of stainless steel, although other materials are also contemplated.

Note that other wire lengths are also contemplated.

The puncture wire 30 in some embodiments has one or more markings on its outer surface to indicate to the surgeon its position with respect to the sheath 20, skin, and/or ureteroscope 40. The markings can be placed on a region of the puncture wire 30 extending outside the body or alternatively or additionally on a region extending within the body to be imaged by the ureteroscope 40. Likewise, the sheath 20 can have one or more markings on a region outside the body, e.g. adjacent sheath locking mechanism 60, or adjacent the pin-vise lock, and/or inside the body where the marking(s) can be visualized by the ureteroscope 40. FIG. 1A illustrates markings 39 on a distal portion of wire 30 and markings 29 on a distal portion of sheath 20 by way of example.

FIG. 12 illustrates one embodiment of a kit containing the system of the embodiment of FIGS. 1-12. In this embodiment, kit 70 includes packaging 72 with portions to receive the puncture wire 30/sheath 20 assembly as well as a space to receive a guidewire. The guidewire 75 replaces the puncture wire 30 during the procedure as will be described in the method of use below. The kit 70 of FIG. 12 can also include a sheath locking mechanism such as sheath locking mechanism 60 described above, mounted to the protective sheath 20, to enable mounting of the sheath 20 to the ureteroscope 40, or provided as a separate component within the kit 70 which the user would mount to the sheath 20 after removing it from the packaging.

Turning now to the method of use of the system of FIGS. 1-11, FIG. 3 illustrates ureteroscope 40 inserted through the ureter U and extending up to the kidney K. The ureteroscope 40 is manipulated under vision so its distal end 45 extends into the calyx of choice, e.g. calyx C1 (FIG. 4). Note the ureteroscope 40 can be articulated into the calyx of choice.

If during insertion of the ureteroscope 40 a stone is encountered under visualization that is blocking the path to the desired calyx C, e.g. calyx C1, C2, C3 etc., a laser fiber (not shown) can be inserted through the working channel 42 of the already positioned ureteroscope 40 to perform laser lithotripsy to reduce the size of the stone to allow access by the ureteroscope 40 to the desired calyx. The laser fiber can then be removed from the working channel 42.

After placement of the ureteroscope 40 at the desired location, e.g. into calyx C1 of FIG. 4, the puncture wire 30 and sheath 20, locked together by tightening of the pin vise lock mechanism 50 as described above, are inserted through the working channel 42 of ureteroscope 40. This initial insertion is illustrated in FIGS. 3 and 4. At this point, the puncture wire tip 32 of puncture wire 30 is retracted and thereby shielded within the protective sheath 20. Note the sheath locking mechanism 60 is mounted to side port 44 e.g. via threaded or snap fit engagement, so the sheath 20 can be later locked to the ureteroscope 40. Sheath 20 extends through the lumen in the locking mechanism 60.

The puncture wire 30 and sheath 20 are then advanced just distal of the tip 45 of the ureteroscope 40 (beyond distal opening 47), and viewed to make sure they are in the desired anatomical position. Once so positioned, the threaded knob 64 of sheath locking mechanism 60 is rotated (see arrow of FIG. 8) to clamp down on the O-ring 68 to reduce its lumen internal diameter, thereby providing a clamping force on the outer wall of sheath 20. This locks the sheath 20 in position, preventing movement with respect to the ureteroscope 40 and easing advancement of the puncture wire for the surgeon.

To next advance the puncture wire 30 further through the scope 40 and sheath 20, actuator 52 of pin vise lock 50 is rotated as described above, thereby releasing the locking engagement of the puncture wire 30 and sheath 20. This enables the surgeon to advance the puncture wire 30 through the kidney K, flank F and skin S as shown in FIGS. 5, 5A and 6.

Once positioned through the flank F and skin S, the sheath 20 is then re-locked in relation to the puncture wire 30 and the two components are advanced further through the working channel 42 of the ureteroscope 40 and through the flank and skin to the position of FIG. 7. Note the puncture wire 30 has been further advanced from its extended position of FIG. 6.

It should be appreciated that alternatively the sheath 30 and puncture wire 20 can be locked together by the pin vise locking mechanism 50, with the puncture tip 32 slightly protruding from the sheath 20, and advanced together through the skin rather than the puncture wire 30 advanced first, followed by advancement of the sheath 20 over the wire 30 as in the steps of FIGS. 6 and 7. In either case, the puncture wire 30 and sheath 20 are advanced through the skin to the position of FIG. 7. Note that the puncture wire 30 is protected along its length by the sheath 20 as well as by the ureteroscope 40.

In the next step, illustrated in FIG. 10, the puncture wire 30 is withdrawn from the sheath 20 in the direction of the arrow which is opposite the direction of insertion of the wire 30 and sheath 20, and out through the working channel 42 and side port 44 of the ureteroscope 40. Note that if the sheath 20 and puncture wire 30 are locked together at this point, the pin vise lock 50 needs to be loosened to allow withdrawal of the puncture wire 30 from the sheath 20. Withdrawing the wire 30 from the patient's body leaves the sheath 20 in place extending through the selected calyx C1 and flank and skin. The ureteroscope 40 is then withdrawn from the body, leaving the sheath 20 in the body, the in situ/in vivo sheath 20 thereby providing a "through and through sheath" as shown in FIG. 11.

A guidewire 75 can then be inserted though the lumen of the sheath 30. The guidewire can be inserted in either a retrograde or an antegrade fashion. Guidewires that can be inserted through the sheath 20 include about 0.020 to about 0.038 inch guidewires. After insertion of the wire 75, the sheath 20 is removed, enabling the wire 75 to obtain "through and through" control of the urinary system.

Thus, as can be appreciated, the protective sheath 20 functions as an "exchange sheath" (or exchange catheter) as after withdrawal of the puncture wire 30 therefrom, it allows for passage of another wire e.g. a 0.020 to 0.038 inch guidewire, the guidewire exchange allowing for subsequent passage of various treatment devices thereover, such as a dilation balloon. That is, the guidewire allows for nephrostomy tract dilation.

The protective sheath 20, as noted above preferably has an outer diameter of about 0.042 inches. However, in alternate embodiments, a larger diameter sheath can be utilized which would exchange for larger diameter wires, allowing for subsequent passage of larger diameter devices.

An alternate embodiment of the system and method of the present invention is illustrated in FIGS. 13-21. In this embodiment, the system includes a sheath 110 and puncture wire 120. The system also includes a second sheath 130.

More specifically, protective sheath 110 has a lumen 112 extending therethrough dimensioned to slidingly receive the puncture wire 120 therein. That is, wire 120 is received within the sheath lumen 112 for sliding movement from a retracted position wherein the puncture (penetrating) tip 122 of wire 120 is protected (shielded) by the sheath 110 (see e.g. FIG. 16) and an extended position where the puncture tip 122 is exposed from the sheath 110 to penetrate tissue (see e.g. FIG. 18). Exposure of the puncture wire 120 enables advancement of the wire 120 through the flank and skin as described below.

The puncture wire 120 and sheath 110 are releasably locked together by a conventional vise lock 150. The pin vise lock 150 functions like the pin vise lock 50 of FIG. 2, and is best illustrated in FIGS. 14 and 17. That is, like pin vise lock 50, pin vise lock 150 has a rotatable actuator 152 and a metal locking tube 154 with a longitudinally extending elongated slot 155. A first (distal) portion 154a of locking tube 154 is seated within tube 156; a second opposite proximal portion 154b is seated within the actuator 152. Actuator 152 has a reduced diameter portion 152a threadingly received in tube 156 and a lumen through which the wire 120 extends. When actuator 152 is rotated within tube 156, it clamps down on the metal locking tube 154 reducing its diameter due to slot 155, to thereby clamp down on the wire 120 to lock it from sliding movement with respect to the sheath 110. That is, as described below with respect to the method of use, the wire 120 and sheath 110 can be locked together so they can be advanced as a unit through the ureteroscope 40. When it is desired to move the puncture wire 120 relative to the sheath 110, the actuator 152 is unscrewed from tube 156, thereby releasing the clamping force on the metal tube 154 so the wire 120 can slide relative to the sheath 110. A reinforcement tube 158 extends distally from tube 159 which connects to tube 156 via screw threads.

The distal portion of tube 159 can include a threaded region which can be threaded directly into the working channel 42 of ureteroscope 40. Alternatively, a snap fit arrangement can be provided to attach the pin vise lock mechanism to the working channel 42. Other methods are also contemplated to attach the locking mechanism 150 to the ureteroscope 40 to thereby lock the sheath 110 to the ureteroscope 40.

The puncture wire 120 of FIG. 13 may have a length shorter than the length of the puncture wire 30 of FIG. 1. For example, the puncture wire 120 preferably has a length of about 135 cm to about 160 cm and can be less than about 145 cm. The sheath 110 of FIG. 13 has a length shorter than the length of the sheath 20 of FIG. 1. For example, the sheath 110 preferably has a length of about 75 cm to about 90 cm and more preferably a length of about 80 cm. Other lengths of the sheath 110 and wire 120 are also contemplated.

The system of the embodiment of FIGS. 13-21 also includes a second sheath 130 designed to replace the first sheath 110 during the procedure. Second sheath 130 preferably has a length of about 85 cm to about 120 cm and more preferably a length of about 100 cm to about 115 cm, an inner diameter of about 0.025 to about 0.045 inches, more preferably from about 0.025 to about 0.038 inches, and an outer diameter of about 0.035 inches to about 0.045 inches, and preferably about 0.042 inches. Other dimensions are also contemplated. As will be explained, in further detail below during the discussion of the method, after the sheath 110/puncture wire 120 assembly are inserted through the ureteroscope 40 and through the flank and skin, the first sheath 110 is withdrawn from the body and the second sheath 130 is inserted through the ureteroscope 40, advanced beyond the distal end of the scope 40 under visualization, locked to puncture wire with a pin vise lock on second sheath and the puncture wire/sheath duo are further advanced through the flank and skin. Note the pin vise is not shown in the drawings on the second sheath 130, it being understood that a pin vise similar to the pin vise of the first sheath can be utilized. Other locking mechanisms can also be utilized. Thus, the puncture wire 120, while being protected within the working channel 42 of the ureteroscope 40, provides a guide for sheath exchange. Note sheath 130 can in some embodiments include a pin vise lock e.g. (similar to mechanism 150) or other locking mechanisms to mount (lock) to the ureteroscope 40.

In some embodiments, a kit is provided containing both sheaths 110, 130. More specifically, as shown in FIG. 22, the kit 160 includes a packaging 165 containing the first sheath 110 and the second sheath 130 for replacing the first sheath 110. Second sheath 130 can include lock 140 to lock to the working channel 42 of the ureteroscope to prevent movement of the sheath 130 with respect to ureteroscope 40. For example, lock 140 can include a threaded or snap fit attachment mechanism.

Turning now to the method of insertion of the system of FIGS. 13-21, and with initial reference to FIG. 15, the ureteroscope 40 is advanced though the ureter and to the kidney K, and its distal tip 45 is inserted into the calyx of choice, e.g. calyx C1, in the same manner as described above with the embodiment of FIGS. 1-13. Note that if during insertion of the ureteroscope 40 a stone is encountered under visualization that is blocking the path to the desired calyx C, a laser fiber (not shown) can be inserted through the working channel 42 of the already positioned ureteroscope 40 to perform laser lithrotripsy to reduce the size of the stone to allow access by the ureteroscope 40 to the desired calyx. This is performed in the same manner as described above in the FIG. 1 embodiment.

The puncture wire 120 and protective sheath 110, locked together by the pin vise lock 150, are then inserted through the side arm 44 and working channel 42 of the ureteroscope 40 as shown in FIG. 16. At this point, the puncture wire tip 122 is retracted within the protective sheath 110. The sheath 110 and puncture wire 120 are then advanced under visualization just distal of the distal end 45 of the ureteroscope 40. Once the positioning of the wire 120 and sheath 110 are confirmed by the surgeon, the pin vise lock 150 is loosened (FIG. 17) by rotating actuator 152 in the same manner as described above with respect to pin vise lock 50, thereby releasing the locking engagement of the puncture wire 120 and sheath 110 and the puncture wire 120 is advanced from the sheath 110 through the kidney K, flank F and skin S to the position shown in FIGS. 18 and 19.

Note that the threaded distal end or other connecting feature of tube 159 is attached to the working channel 42 to lock the sheath 110 against movement with respect to the ureteroscope 40 once the sheath 110 is advanced slightly distal of the end 45 of the ureteroscope 40. Other locking mechanisms can also be provided, and positioned on other regions of the sheath, e.g. proximal or distal of pin-vise lock 150.

It should be appreciated that the sheath 110 and puncture wire 120 can be locked together by the pin vise locking mechanism 150, with the puncture tip 122 slightly protruding from the sheath 110, and advanced together through the skin or alternatively, the wire 120 can be advanced first, followed by advancement of the sheath 110 over the wire 120. In either case, the puncture wire 120 and sheath 110 are advanced through the skin. Note that except for the exposed portion beyond the calyx, the wire 120 is protected along its length by the sheath 110 as well as by the ureteroscope 40.

Once positioned through the flank F and skin S, the sheath 110 is then removed from working channel 42 in the direction opposite the direction of insertion of the sheath 110. This leaves the puncture wire 120 extending through the working channel 42 of the ureteroscope 40, protected by the ureteroscope 40 as shown in FIG. 20. Next, a second sheath 130 is inserted over the puncture wire 40. The second sheath 130 can be inserted in a retrograde fashion (in the same direction as the first sheath 110) over the wire 120 and through the working channel 42 of the ureteroscope 40, or alternatively, if not provided with an attached vise lock, inserted in an antegrade fashion over the puncture wire 120 and into and through the working channel 42 of the ureteroscope.

It is contemplated that if the second sheath 130 does not include a vise lock after antegrade or retrograde insertion, a separate lock can be attached after insertion through the working channel 42 to lock the sheath 130 and puncture wire 120 together and/or lock the sheath 130 to the ureteroscope 40 at the side port 44. After insertion of the second sheath 130 and advancement out the flank, the puncture wire 130 is removed from the lumen 131 of sheath 130, preferably in a direction opposite the direction of its initial insertion through the ureteroscope 40, although it can be removed in the same direction. This leaves the second sheath 130 in position to receive a guidewire therethrough, e.g. guidewire 170 of FIG. 21. Guidewire 170 can be inserted in either direction through lumen 131 of sheath 130. After insertion of the guidewire, the second sheath 130 is removed, leaving the guidewire 170 to extend "through and through."

Note the ureteroscope 40 can be removed after insertion of the second sheath 130 or alternatively after insertion of the guidewire 170 following removal of the puncture wire 120 from sheath 110.

It is also contemplated that in an alternate embodiment, the puncture wire can be utilized without a protective sheath and inserted directly into the ureteroscope 40. The working channel 42 of the ureteroscope in this embodiment would thereby protect the puncture wire during insertion. This would reduce the number of components. Such sheathless puncture wire would then require subsequent insertion of a sheath thereover to provide access through the flank F and skin S. Such sheathless puncture wire can be utilized with either method disclosed herein or with antegrade passage of the sheath through the flank over the puncture wire.

In these sheathless embodiments, the puncture wire can be locked to the operating (working) channel 42 of the ureteroscope 40 during insertion of the ureteroscope 40 into the calyx, and then the puncture wire released from locking engagement with the ureteroscope 40 to enable advancement distal of the end of the ureteroscope through the flank and skin. Such locking can be achieved with a vise lock or a locking mechanism similar to locking mechanism 60 described above, with the O-ring clamping on the puncture wire. Such embodiments enable a larger diameter puncture wire to be utilized, which could enable passage of a dilation balloon or other treatment devices directly over the puncture wire, thereby obviating the need for an exchange catheter and a second wire.

It is also contemplated that the characteristics of the puncture wire can be altered. For example, a coating can be applied to improve lubriciousness, and such coating can extend on a portion of or the length of the wire proximal of the tissue puncturing region. Coating with a low friction coefficient material could increase the wire caliber without significantly changing its handling properties. Preferably, the coating would not be applied to the distal 20-30 cm of the wire that is used to puncture the kidney, flank and skin.

Also, in some embodiments, portions of the wire can be made thicker, softer or more flexible. For example, the wire can have a thinner portion at the distal portion with a larger diameter at the remaining portion such as the region that contacts and traverses the ureteropelvic junction. This is shown for example in FIG. 23 where puncture wire 220 has a distal region 221 of a smaller diameter than proximal region 223.

The protective sheath for the puncture wire may be constructed to be thin walled to permit the entire puncture wire/protective sheath duo to maintain a small enough total diameter for passage through the working channel of ureteroscope. Use of materials such as polyimide for sheath construction may have beneficial properties for this application.

It should be appreciated that nephrostomy tract dilation could be performed over the puncture wire itself, where the puncture wire may be a single or variable property wire. In this technique, after successful passage of the puncture wire out the flank either with our without the aid of a sheath, the puncture wire is, in fact, not exchanged for a working wire. Rather, the puncture wire itself is suitable for dilation of the nephrostomy tract over the puncture wire. If a variable property puncture wire is utilized, it is possible that a length of wire is further advanced out the flank, and/or a length of wire is removed from a delivered portion of the puncture wire at the flank, such that nephrostomy dilation is performed over a segment of the puncture wire having properties different than the portion of the puncture wire that penetrated the flank/skin. This technique may be utilized with a larger caliber puncture wire, if desired.

Figure 24A:
FIG. 24A is a side view of an alternate embodiment of the protective sheath.

To enhance functionality of the protective sheath, the distal tip of the protective sheath may be constructed with a gentle bend such as sheath 250 of FIG. 24A having a distal bent region 252. This would provide the urologist with improved ability to direct the path of the puncture wire through the flank. With a Tuohy-Borst style working channel port such as in FIG. 3 that allows circumferential locking of the outer sheath in relation to the scope, the exact length of the outer sheath that passes out of the ureteroscope tip can be achieved and maintained by the urologist, by engaging the Tuohy-Borst lock around the sheath after passing the sheath out of the end of the ureteroscope 40. Depending on the length of the outer sheath that is advanced out of the ureteroscope tip, less or more 'bend' of the sheath will be exposed, and the path of the puncture wire 260 can thus be better controlled.

Figure 24B:
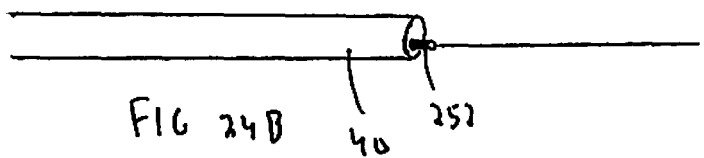
FIGS. 24B and 24C illustrate the sheath of FIG. 24A exposed different distances from the ureteroscope.
Figure 24C:
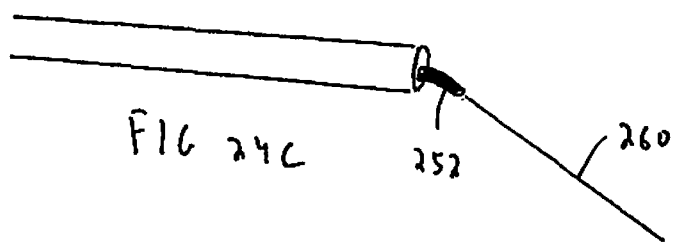

Thus, as can be appreciated, if less of the sheath 250 is advanced from the end of the ureteroscope 40, a straighter wire path in relation to the end of the ureteroscope achieved (see FIG. 24B). If more of the sheath 250 is delivered, a few degrees of wire deflection will be achieved by virtue of the bend in the end 252 of the sheath 250 (see FIG. 24C). One example of how this may be beneficial is the urologist may be able to achieve a more posterior path for wire puncture by extending several millimeters of sheath out of the ureteroscope tip.

Precise angulation of the tip of the exposed sheath 250 can be achieved by twisting the pin-vise apparatus with the Tuohy-Borst in a loosened position. With an axial twist-resistant design of the protective sheath, any twist of the pin-vise lock would be reflected in the angulation of the exposed tip of the sheath just beyond the end of the ureteroscope 40.

Alternately, the sheath could be constructed of a coaxial design.

The sheath may be constructed or post-processed to have enhanced visibility under, ultrasound imaging. This may be achieved by any number of techniques, which may include but are not limited to placing a ceramic, graphite, Teflon, tungsten, Nitinol or platinum tip or outer coating on all or part of sheath or creating with or post-processing the sheath using laser or other abrasing or cutting technology to create small or microscopic grooves or indentations/dimples in the outer surface of the sheath to increase echogenicity.

It is also contemplated that all or part of the puncture wire and/or the exchange wire may be designed to have enhanced ultrasound visibility. This may allow for reduced radiation exposure during nephrostomy creation by allowing ultrasound guided confirmation of wire location during deployment. Options to achieve this include, but are not limited to the following: 1) Constructing the puncture wire and/or the exchange wire entirely of, or with a component of, a highly ultrasound-visible metal or other material. Examples include, but are not limited to, cobalt/chromium, graphite, Teflon, platinum or tungsten. These components may be mixed with stainless steel as an alloy or simply the distal tip of the wire can be made of these materials. 2) Coating the puncture wire and/or exchange wire with ceramic material, graphite, Teflon, tungsten, platinum, other metals or polymers, or material impregnated with microbubble technology such as glass microspheres, air microbubbles, or other adherent echogenic polymeric films. 3) The puncture wire and/or exchange wire may be constructed with or post-processed to create uneven surface(s) such as by brushing, lasering, creating indentations or cutting the outer surface of the wire. This would increase echogenicity of the wire.

With reference to FIGS. 25-31, a system and method is disclosed to facilitate exchange of a puncture wire for a working wire after the puncture wire has been advanced through the flank and skin as described in the embodiments above and the protective sheath and ureteroscope have been withdrawn. In this system, a coaxial catheter is passed antegrade over the exposed penetrating tip of the puncture wire through the fascia and renal capsule, and then following over the puncture wire down the ureter.

Turning first to FIG. 25A, the system includes a coaxial catheter, or coaxial transitional dilator, designated generally by reference numeral 310 and having a proximal portion 313 and a distal portion 315. The coaxial catheter 310 includes an inner catheter 314 positioned within a concentric outer catheter 312. Preferably, there is close to zero tolerance between the coaxial catheters 312, 314 to facilitate passage of the catheter (dilator) 310 through the fascia and renal capsule. The coaxial catheter 310 preferably has a length of between about 10 cm and about 50 cm, and more preferably between about 20 cm and about 35 cm. Other dimensions are also contemplated.

The inner catheter 314 is dimensioned to closely match the outer diameter of the puncture wire 230 as it is configured for passage antegrade over the puncture wire 230. For example, if the outer diameter of the puncture wire 230 is 0.017 inches, the inner diameter of the inner catheter 314 would be only slightly larger, such as 0.018 inches, i.e. slightly larger to enable smooth passage over the puncture wire 230 but small enough to provide little clearance between the two components. Such minimized clearance reduces the likelihood of tearing of tissue during advancement over the puncture wire 230, reduces the likelihood of tissue being caught between the edges of the catheter 310 and the puncture wire 230, and reduces the likelihood of the catheter 310 getting caught and thereby failing to obtain access. That is, the inner catheter 314 is dimensioned to provide lower resistance antegrade passage over the puncture wire 230. Note the inner catheter 314 can have a tapered tip 317 at the distal end. Distal opening 319 at the distal tip 317 is slid over the penetrating tip of the puncture wire 230 as described in the method of use below. Note the puncture wire of this embodiment, designated by reference numeral 230, is identical to puncture wires 30 and 130 discussed above. Similarly, sheath 220 of this embodiment is identical to sheath 20 and 110 discussed above.

The outer catheter 312 preferably has an inner diameter large enough to pass at least a 0.035 inch guidewire once the inner catheter 314 is removed from therein (and the puncture wire 230 is also removed). Thus, the outer catheter 312 preferably has an inner diameter of about 0.020 inches to about 0.055 inches, and more preferably about 0.040 inches.

In an alternate embodiment, the outer catheter 312 is dimensioned to have a sufficiently large inner diameter to accept two wires, such as two wires ranging from about 0.025 inches to about 0.038 inches in diameter. Thus, the outer catheter 312 is such embodiments can have an inner diameter of about 0.050 inches to about 0.090 inches, and more preferably about 0.070 inches. The ability to accept two working wires enables direct nephrostomy dilation over one of the wires, with the second wire secured as a safety wire in case of displacement of the working or dilation wire. This ability to accept two wires is illustrated in FIG. 30, where the first guidewire 401 and the second guidewire 402 are inserted through the outer catheter after removal of the inner catheter. In FIG. 30, the outer catheter has been removed.

As shown in FIG. 25A, inner and outer catheters 312, 314 are preferably secured together at the proximal portion 313 so they can be advanced as a unit over the puncture wire 230. One method of attachment is a conventional luer lock, designated by reference numeral 320, although other methods of attachment are also contemplated. The catheters 312, 314 are consequently inserted over the puncture wire 230 secured together, and then the luer 320 is unlocked to remove the inner catheter 314 from the outer catheter 312 (in a retrograde fashion), leaving the outer catheter 312 in place as described below.

In the alternate embodiment of FIG. 25B, the coaxial catheter 340 includes an inner catheter 344 and an outer catheter 342 which remain separate components and do not lock together. Inner catheter 344 has a proximal portion 347 and a distal portion 349; outer catheter 342 has a proximal portion 346 and a distal portion 348. In this embodiment, first the inner catheter 344 is passed antegrade over the puncture wire, functioning as an obturator for passage antegrade of the outer catheter 342 thereover into the ureter. After passage of the outer catheter 342 over the inner catheter 344, the inner catheter 344 is removed in the direction opposite the insertion direction, leaving the outer catheter 342 in place in the same manner outer catheter 312 remains in place in the method described below. Note in this embodiment, the inner catheter 344 is dimensioned the same as the inner catheter 314 of the embodiment of FIG. 25A to provide low resistance to passage into the ureter. The outer catheter 342 can be also be dimensioned the same as outer catheter 312 of FIG. 25A, e.g. within the range of about 0.020 inches to about 0.090 inches, to allow reception of one wire or of more than one wire e.g. a guidewire and a safety wire. The lumen of the outer catheter 342 would closely match the outer diameter of the inner catheter 344 to minimize clearance.

A larger inner diameter of the outer exchange coaxial catheter 310 can be achieved in one embodiment by constructing the catheter of a thinner wall, such as a polyimide material.

Note the distal tip of the catheters 312, 314 (and 342, 344) can be radiopaque for localizing by fluoroscopy. To enhance imaging, additional regions of the catheter can be composed of radiopaque material, and even the entire length of the catheter.

The catheter 310 (or 340) may be constructed or post-processed to have enhanced visibility under ultrasound imaging. This may be achieved by any number of techniques, which may include but are not limited to placing a ceramic, graphite, Teflon, tungsten, Nitinol or platinum tip or outer coating on all or part of the catheter or creating with or post-processing the catheter using laser or other abrasing or cutting technology to create small or microscopic grooves or indentations/dimples in the outer surface of the catheter to increase echogenicity.

The method of use of the coaxial catheter 310 will now be described. The coaxial catheter 310 is utilized after the puncture wire 230 is advanced through the ureteroscope 40 and out of the flank and skin in the manner described above and illustrated in FIG. 26. In short, the coaxial catheter 310 is utilized after the following steps which were described in detail above with the first and second systems: a) the flexible ureteroscope is passed through the ureteral access sheath into the calyx of choice for nephrostomy creation (see e.g. FIG. 3); b) the puncture wire and protective (insulating) sheath are passed into the ureteroscope working channel while maintaining the tip of the ureteroscope in the calyx of choice (the sheath can be secured to the ureteroscope as in FIG. 5); c) the sheath and puncture wire are advanced from the distal opening of the ureteroscope (FIG. 5; and d) the pin vise lock is opened and the puncture wire is advanced with respect to the sheath until fluoroscopic vision shows the puncture wire tenting the flank/skin or emerging therefrom. Once the puncture wire tract is evaluated as safe for tract (e.g. not too cephalad or anterior), at the flank, the wire is grasped and gently drawn outside of the flank (See e.g. FIG. 5A). These are the steps described above and illustrated in the embodiment of FIGS. 1-12 and in the embodiment of FIGS. 13-22.

Note the puncture wire may have markings as described above. For example, as shown in FIG. 26a one or more markings 234 at a distal portion of the puncture wire 230 would be visible when the wire 230 is advanced through the flank and skin to inform the user of the exact length of the puncture wire 230 that is outside the flank. One or more markings 236 can also be positioned at the proximal end of the puncture wire 230 which extends outside (proximal) of the ureteroscope 40. The markings can be spaced for example at 10 cm intervals, although other intervals can be utilized. Different indicia can also be utilized, such as one mark for 10 cm, two marks for 20 cm, three marks for 30 cm, etc. Clearly other indicia and alternate number of markings are contemplated.

Returning now to the method steps of the system of FIGS. 25-31, after the puncture wire 230 is advanced through the flank and skin, the flexible ureteroscope and puncture wire sheath can be removed from the patient, or alternately can be left in situ as in FIG. 26. The skin is cut several millimeters with a scalpel at the site of the puncture wire penetration. If the puncture wire tip became bent (see region 233 of FIG. 27), it is straightened or cut off with a conventional wire cutter C. Fascia may be incised or can be left as is, i.e. not separately incised. If performed as a separate step, fascial incision can be performed either with a scalpel passed alongside the puncture wire or with the fascial incising needle passed over the puncture wire.

Figure 29:
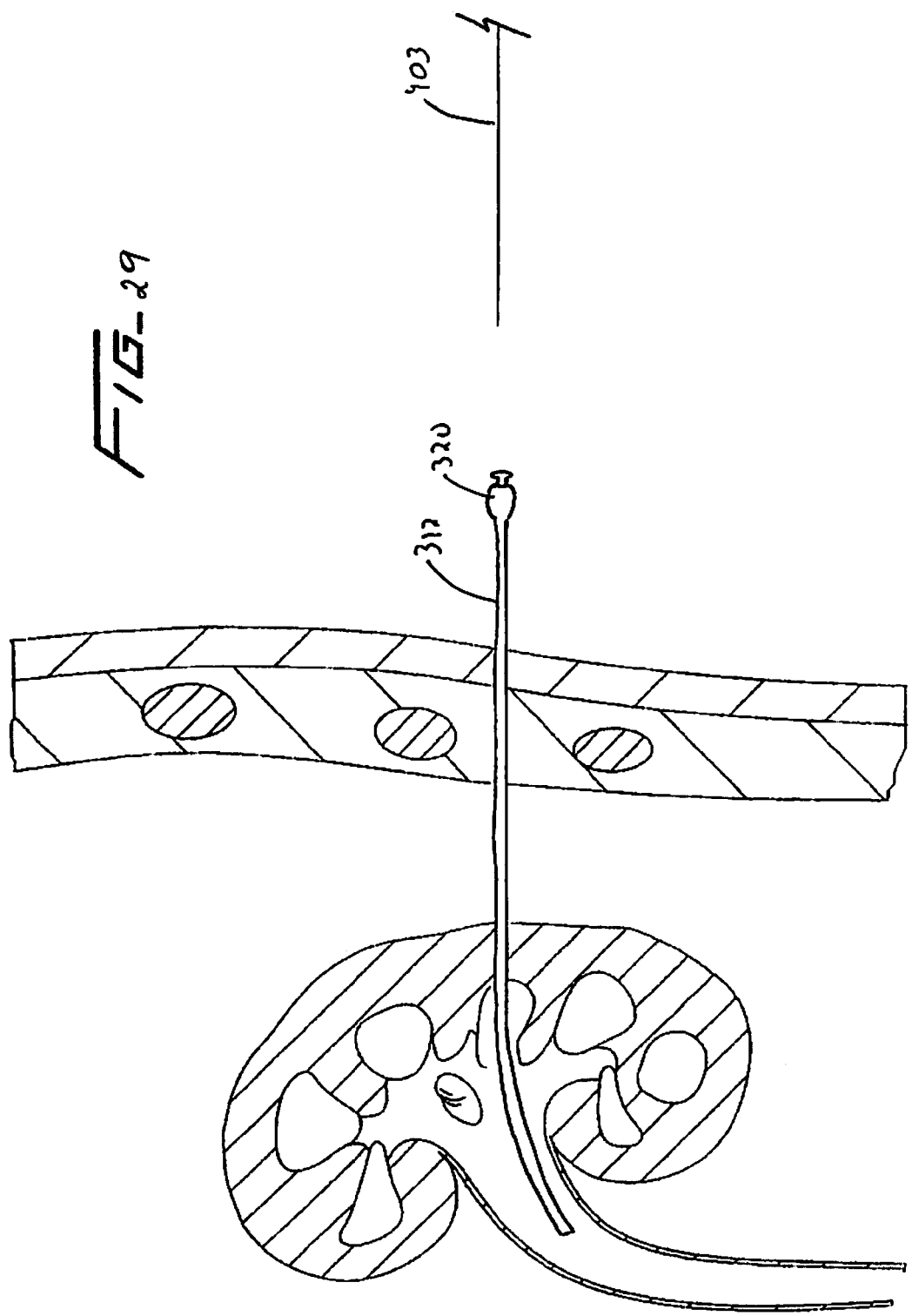
FIG. 29 is a view similar to FIG. 28, illustrating the puncture wire and the inner catheter of the coaxial catheter removed, leaving the outer catheter of the coaxial catheter in place, and further showing a replacement guidewire for passage antegrade though the outer catheter.

Then the coaxial catheter 310 is loaded over penetrating tip 235 of puncture wire 230 exposed at the flank and passed into the kidney and down into the ureter as shown in FIG. 28. The puncture wire 230 and the inner catheter 314 of the coaxial catheter 310 are removed, leaving the outer catheter 312 in place as shown in FIG. 29. A replacement guidewire 403 is inserted through the proximal opening of the outer catheter 312 in the direction of the arrow of FIG. 29 and passed antegrade through the lumen of the outer catheter 312 under fluoroscopic guidance. The outer catheter 312 would then be removed leaving the wire in place for nephrostomy dilation as the wire is advantageously "through and through" and out the urethra.

Optionally, the outer catheter can be configured as described above to receive two wires wherein a first guidewire 401 and a safety guidewire 402 are inserted antegrade through the outer catheter 312'. The outer catheter 312' of FIG. 29 is then removed, leaving the two wires 401, 402, in place as shown in FIG. 30, enabling nephrostomy dilation due to the "through and through" wire.

In the embodiment utilizing the coaxial catheter of FIG. 25, the inner catheter 344 would be inserted first over the puncture wire 230, followed by insertion of the outer catheter 342 thereover. The inner catheter 344 and puncture wire 230 would be then be removed, leaving the outer catheter 342 in place to receive one or more wires in the same manner as catheter 312. In all other respects, the method of use is the same as described above.

To create a nephrostogram to identify renal pelvis anatomy during balloon dilation of nephrostomy tract, the ureteral safety guidewire placed during the ureteroscopy portion of the procedure can be exchanged for a ureteric catheter through the urethra. Retrograde nephrostogram is performed through the uretereic catheter. A Foley catheter is placed in the bladder.

A kit can also be provided as shown in FIG. 31. The kit 370 includes the puncture wire 230 with protective sheath and the coaxial transitional dilating catheter 310 (or alternatively 340). The kit can further include a Tuohy-Borst adaptor for the working channel of the ureteroscope and/or one or more guidewires for exchange with the puncture wire once the coaxial catheter 310 (or 340) is placed as described herein. A wire cutter can also be included in the kit.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A method for exchanging a puncture wire for a working wire in creating a tract for nephrostomy tube creation comprising the steps:
   a) providing a puncture wire having a tissue penetrating tip shielded in a sheath, the puncture wire slidable within the sheath and releasably lockingly engaged thereto and the sheath retractable with respect to the puncture wire in an antegrade direction;
   b) inserting the puncture wire and sheath in a retrograde direction through a working channel of an ureteroscope to exit a channel of the ureteroscope;
   c) releasing the puncture wire from the sheath;
   d) advancing retrograde the puncture wire from within a selected calyx through a flank of a patient;
   e) inserting over the puncture wire in the antegrade direction a flexible coaxial catheter having a length of between about 20 cm to about 50 cm, the coaxial catheter having an outer catheter and an inner catheter, the outer catheter positioned over the inner catheter, and the coaxial catheter inserted into the ureter, the coaxial catheter inserted over the puncture wire so that the flexible coaxial catheter is a first member inserted over an exposed penetrating tip of the puncture wire after the penetrating tip of the puncture wire extends from the flank of the patient;
   f) removing the puncture wire and inner catheter from the coaxial catheter; and
   g) inserting a wire in the antegrade direction through the coaxial catheter.

2. The method of claim 1, further comprising the step of inserting another wire in the antegrade direction through the coaxial catheter.

3. The method of claim 2, further comprising the step of removing the puncture wire and the inner catheter prior to the step of inserting the wire.

4. The method of claim 2, wherein the puncture wire has at least one marker thereon to indicate an extent of advancement relative to a patient's skin.

5. A method for exchanging a puncture wire for a working wire in creating a tract for nephrostomy tube creation comprising the steps:
   a) providing a puncture wire having a proximal section, a distal section and a distalmost tissue penetrating tip extending from the distal section, the distal section being proximal of the penetrating tip, the tissue penetrating tip shielded in a sheath, the puncture wire slidable within the sheath and releasably lockingly engaged thereto, the proximal section of the puncture wire having a first cross-sectional dimension and the distal section of the puncture wire having a second cross-sectional dimension, the second cross-sectional dimension being less than first cross-sectional dimension;
   b) inserting the puncture wire and sheath in a first retrograde direction through a working channel of an ureteroscope to exit a channel of the ureteroscope, a portion of the puncture wire being deflectable by deflection of a distal tip of the ureteroscope;
   c) releasing the puncture wire from the sheath and advancing the puncture wire a first distance from the sheath;
   d) advancing the puncture wire from a selected calyx through a flank of a patient such that the puncture wire extends outside the patient, a portion of the proximal section of the puncture wire remains inside the body exposed across a ureteropelvic junction so that the larger cross sectional dimension of the proximal section of the puncture wire provides a larger and less traumatic contact surface with the ureteropelvic junction during subsequent advancement of a flexible catheter over the puncture wire, the proximal section having a diameter between 0.020 inches and 0.045 inches;
   e) retracting the sheath thereby exposing the proximal section of the puncture wire to the ureteropelvic junction;
   f) after the step (d) of advancing the puncture wire, inserting the catheter in either the first direction or a second direction, the catheter extending into the ureter; and
   g) inserting a wire in the second direction through the catheter.

6. The method of claim 5 wherein the puncture wire has a material over the proximal section to provide an increased first cross-sectional dimension of the proximal section relative to the distal section.

7. The method of claim 5, wherein the distal section of the puncture wire is tapered to form a decreased cross-sectional dimension of the distal section relative to the proximal section.

8. The method of claim 5, wherein the puncture wire includes a wire coil placed around the proximal section and not around the distal section to provide an increased first cross-sectional dimension of the proximal section relative to the distal section.

9. A method for creating a tract in retrograde fashion for nephrostomy tube creation comprising the steps:
   a) providing a puncture wire having a proximal section, a distal section and a distalmost tissue penetrating tip extending from the distal section, the distal section being proximal of the penetrating tip, the tissue penetrating tip shielded in a sheath, the puncture wire slidable within the sheath and releasably lockingly engaged thereto, the sheath being retractable with respect to the puncture wire in an antegrade direction;
   b) inserting the puncture wire and sheath in a first retrograde direction through a working channel of an ureteroscope to exit a channel of the ureteroscope, the puncture wire being deflectable by deflection of a distal tip of the ureteroscope;
   c) releasing the puncture wire from the sheath and advancing the puncture wire a first distance from the sheath,
   d) advancing the puncture wire from within a selected calyx through a flank of a patient such that a portion of the puncture wire extends outside the patient, the puncture wire having a diameter at a proximal section of between 0.020 inches and 0.045 inches, the diameter at the proximal section being greater than a diameter of the distal section which is proximal of the penetrating tip, the proximal section of the puncture wire remains inside the body exposed across a ureteropelvic junction so that the proximal section of the puncture wire provides a sufficient and less traumatic contact surface with the ureteropelvic junction during subsequent advancement of a flexible catheter over the puncture wire;
   e) after the step (d) of advancing the puncture wire, inserting the flexible catheter in either the first direction or a second direction, the catheter extending into the ureter.

* * * * *